(12) United States Patent
Mintchev et al.

(10) Patent No.: US 6,243,607 B1
(45) Date of Patent: Jun. 5, 2001

(54) GASTRO-INTESTINAL ELECTRICAL PACEMAKER

(75) Inventors: Martin P. Mintchev, Calgary; Kenneth L. Bowes, Edmonton, both of (CA)

(73) Assignee: University Technologies International Inc., Alberta (CA)

(*) Notice: Subject to any disclaimer, the term of this patent is extended or adjusted under 35 U.S.C. 154(b) by 0 days.

(21) Appl. No.: 09/254,364

(22) PCT Filed: Sep. 4, 1997

(86) PCT No.: PCT/CA97/00616
§ 371 Date: Jun. 7, 1999
§ 102(e) Date: Jun. 7, 1999

(87) PCT Pub. No.: WO98/09679
PCT Pub. Date: Mar. 12, 1998

Related U.S. Application Data
(60) Provisional application No. 60/025,500, filed on Sep. 5, 1996.

(51) Int. Cl.$^7$ .................................................. A61N 1/36
(52) U.S. Cl. ............................................. 607/40; 607/133
(58) Field of Search .................................. 607/40, 41, 2, 607/118, 116, 124, 133

(56) References Cited

U.S. PATENT DOCUMENTS

| | | |
|---|---|---|
| 3,543,761 | 12/1970 | Bradley . |
| 3,646,940 | 3/1972 | Timm et al. . |
| 3,941,136 | 3/1976 | Bucalo . |
| 4,607,639 | 8/1986 | Tanagho et al. . |
| 5,690,691 * | 11/1997 | Chen et al. . |

FOREIGN PATENT DOCUMENTS

| | | |
|---|---|---|
| WO9213592 | 8/1992 | (WO) . |
| WO9401172 | 1/1994 | (WO) . |

OTHER PUBLICATIONS

Bellahsene, B.E., C.D. Lind, B.D. Schirmer, O.L. Updike, and R.W. McCallum, "Acceleration of gstric emptying with electrical stimulation in a canine model of gastroparesis," *Am. J. Physiol.* 262 (5 Pt 1): G826–34, 1992.

Berger, T., J. Kewenter and N.G. Kock, "Response to Gastrointestinal Pacing: Antral, Duodenal and Jejunal Motility in Control and Postoperative Patients," *Annals of Surgery* 164: 139–44, 1965.

Chen, J.D., B.D. Schirmer, and R.W. McCallum, "Serosal and cutaneous recordings of gastric myoelectrical activity in patients with gastroparesis," *Am. J. Physiol.* 266 (1 Pt 1): G90–8, 1994.

Daniel, E.E. and S.K. Sarna, "Distribution of Excitory Vagal Fibers in Canine Gastric Wall to Control Motility," *Gastroenterology* 71:608–13, 1976.

Familoni, B.O., T.L. Abell, G. Voeller, A. Salem, O. Gaber, and D. Nemoto, "Long-term electrical stimulation of the human stomach," *Gastroenterology.* 106 (2) : A496, 1994.

(List continued on next page.)

*Primary Examiner*—Kennedy Schaetzle
(74) *Attorney, Agent, or Firm*—Rodman & Rodman

(57) ABSTRACT

A device and method for electrical stimulation of a portion of the gastro-intestinal tract, defining a longitudinal axis. A proximal and at least one distal electrode set are arranged circumferentially about the portion of the gastro-intestinal tract in a plane substantially perpendicular to the longitudinal axis and in axially spaced relationship relative to each other. At least one power source provides an electrical stimulus to the electrode sets sufficient to stimulate the smooth muscle to produce a local circumferential contraction at each electrode set. A timing mechanism phase locks the electrical stimulus such that it is applied to the electrode sets successively and repetitively. The axially spaced relationship between the electrode sets and the timing of the electrical stimulus are selected such that the local circumferential contractions are artificially propagated distally through the portion of the gastro-intestinal tract.

59 Claims, 11 Drawing Sheets

OTHER PUBLICATIONS

Familoni, B.O.,T.L. Abell, D. Nemoto, G. Voeller and B. Johnson, "Efficacy of electrical stimulation at frequencies higher than basal rate in canine stomach," *Digestive Diseases and Sciences* 42: 892–897, 1997.

Sarna, S.K., K.L. Bowes, and E.E. Daniel, "Gastric Pacemakers," *Gastroenterology* 70: 226–31, 1976.

The GEMS Group, "Electricial stimulation for the treatment of gastroparesis—preliminary report of a multicenter international trial," Abstract from Proceedings of the Fourth International Workshop on Electrogastrography, held May 23, 1996, p. 24.

Familoni, B.,T.Abell, Prem, S. Moolchandani,.G. Voeller, "Optimum Frequency for Stimulating Canine Gastric Electrical Activity," Abstract from Proceedings of the Fourth International Workshop on Electrogastrography, held May 23, 1996, p.23.

Familoni, B.,T. Abell, S. Bhaskar, G. Voeller, "Evaluation of Gastric Electrical Stimulation in Patients with PEGs, " Abstract from Proceedings of the Fourth International Workshop on Electrogastrography, held May 23, 1996, p.22.

Familoni, B., T. Abell, Z. Gan, G. Voeller, "Computer Simulation for Predicting Efficient Gastric Electrical Stimulation," Abstract from Proceedings of the Fourth International Workshop on Electrogastrography held May 23, 1996, p. 21.

Chen, J.D.Z., Z.Y. Lin, B.D. Schirmer, R.D. Williams, B. Ross and R.W. McCallum, "Effect of gastric pacing with optimal parameters on gastric emptying in patients with gastroparesis," In: Proceedings of XV Int. Sumposium on Gastrointestinal Motility, p.42, Rome, Italy, Oct. 1995.

Bilgutay, A.M., R. Wingrove, W.O. Griffin, R.C. Bonnabeau and C.W. Lillehei, "Gastro–intestinal Pacing. A New Concept in the Treatment of Ileus," *Ann. Surg.*, 158: 338–48, 1963.

Kelly, K.A. and C.F. Code, Duodenal–gastric reflux and slowed gastric emptying by electrical pacing of the canine duodenal pacesetter potential, *Gastroenterol.*, 72: 429–33, 1977.

Mirrizzi, N., R. Stella, U. Scafoglieri, "A Model of extra cellular wave shape of the gastric electricial activity," Med. Biol. Eng. & Comput, 23:33–37, 1985.

Mirrizzi, N., R. Stella, U. Scafoglieri, "Model to stimulate the gastric electricial control and response activity on the stomach wall and on abdominal surfact," *Med. Biol. Eng. &Comput*, 24: 157–63, 1986.

Mintchev, M.P. and K.L. Bowes, "Conoidal Dipole Model of the Electricial Field Produced by the Human Stomach," *Med. Biol. Eng. &Comput.*, 33:179–85,1995.

Quast, D.C., A.C. Beall and M.E. DeBakey, "Clinical Evaluation of the Gastrointestinal Pacer," *Surg. Gynec. Obstet.*, 120: 35–37, 1965.

Miedema, B.W., M.G. Sarr and K.A. Kelly, "Pacing the Human Stomach," *Surgery* 111: 143–50, 1992.

Hocking, M.P., S.B. Vogel and C.A. Sininsky, "Human Gastric Myoelectric Activity and Gastric Emptying Following Gastric Surgery and With Pacing," *Gastroenterology* 103: 1811–16, 1992.

Eagon, J.C., and K.A. Kelly, "Effect of electrical stimulation on gastric electrical activity, motility and emptying," *Neurogastroenterology &Motility*, 7:39–45, 1995.

Christensen, J., "Responses of the Smooth Muscle Segment of the Oppossum Esophagus to Distention and Electrical Stimulation, and their Modification by Antagonists," In: Gastrointestinal Motility. International Symposium on Motility of the Gastrointestinal Tract, pp. 167–174, Erlangen, Jul. 15 and 16, 1969.

* cited by examiner 1  2

|  | SPONTANEOUS EMPTYING<br>T1/2 (AVERAGE±SD) | STIMULATED EMPTYING<br>T1/2 (AVERAGE±SD) |
| --- | --- | --- |
| DOG 1 | 38.6±4.2 MIN. | 2.7±0.4 MIN. |
| DOG 2 | 22.6±3.1 MIN. | 4.0±1.0 MIN. |
| DOG 3 | 48.4±6.8 MIN. | 9.4±1.9 MIN. |
| DOG 4 | 31.3±3.2 MIN. | 4.7±0.3 MIN. |
| DOG 5 | 16.5±18.4 MIN. | 9.3±4.0 MIN. |
| DOG 6 | 13.3±1.2 MIN. | 11.3±7.2 MIN. |
| DOG 7 | 19.3±6.8 MIN. | 6.8±2.3 MIN. |
| DOG 8 | 12.3±5.13 MIN. | 5.6±1.15 MIN. |

GASTRO-INTESTINAL ELECTRICAL PACEMAKER

CROSS REFERENCE TO RELATED APPLICATION

This Application claims the benefit of United States of America Provisional Application No. 60/025,500 filed Sep. 5, 1996.

FIELD OF INVENTION

This invention relates to a device for electrical stimulation of smooth muscle comprising a portion of the gastro-intestinal tract, a method for using the device of the within invention and a method for electrical stimulation of the smooth muscle.

BACKGROUND OF THE INVENTION

Many different ways of stimulating gastro-intestinal function have been explored, including pharmacological, neural, purely electrical, and combined methods. In particular, gastric electrical stimulation has been a subject of research investigation for many years (Bellahsene, B. E., C. D. Lind, B. D. Schirmer, O. L. Updike, and R. W. McCallum, "Acceleration of gastric emptying with electrical stimulation in a canine model of gastroparesis" *Am. J. Physiol.* 262(5 Pt 1):G826–34, 1992; Berger, T., J. Kewenter, and N. G. Kock, "Response to Gastrointestinal Pacing: Antral, Duodenal and Jejunal Motility in Control and Postoperative Patients" *Annals of Surgery* 164:139–44, 1965; Chen, J. D., B. D. Schirmer, and R. W. McCallum "Serosal and cutaneous recordings of gastric myoelectrical activity in patients with gastroparesis" *Am. J. Physiol.* 266(1 Pt 1):G90–8, 1994; Daniel, E. E. and S. K. Sarna "Distribution of Excitory Vagal Fibers in Canine Wall to Control Motility" *Gastroenterology* 71:608–13, 1976; Familoni, B. O., T. L. Abell, G. Voeller, A. Salem, O. Gaber, and D. Nemoto "Long-term electrical stimulation of the human stomach" *Gastroenterology* 106 (2):A496, 1994; Sarna, S. K., K. L. Bowes, and E. E. Daniel "Gastric Pacemakers" *Gastroenterology* 70:226–31, 1976).

It is now well known that gastric contractions are controlled by gastric electrical activity ("GEA") (Sarna et. al., 1976). Moreover, when contractions are present, their temporal and propagation organization is strongly related to the organization of GEA. Therefore, electrical stimulation of the stomach may have particular application to a condition known as gastroparesis, in which the stomach is incapable of grinding, mixing and transmitting the food to the duodenum, and to other conditions in which gastric emptying time is abnormally delayed (Bellahsene et. al., 1992; Chen et. al., 1994).

Recently, gastric electrical pacemaking has once again become a subject of intensive investigation (Eagon J C and Kelly K A "Effect of electrical stimulation on gastric electrical activity, motility and emptying" *Neurogastroenterology & Motility.* 7:3945, 1995; The GEMS Group "Electrical stimulation for the treatment of gastroparesis—preliminary report of a multicenter international trial" *Gastroenterology,* 110:A668, 1996; Chen J D Z, Lin Z Y, Schirmer B D, Williams R D, Ross B and McCallum R W "Effect of gastric pacing with optimal parameters on gastric emptying in patients with gastroparesis" In: Proceedings of XV Int. Symposium on Gastrointestinal Motility, p. 42, Rome, Italy, October 1995).

In 1963, Bilgutay et. al. (Bilgutay A M, Wingrove R, Griffin W O, Bonnabeau R C and Lillehei C W "Gastro-intestinal Pacing. A New Concept in the Treatment of Ileus" *Ann. Surg.,* 158;338–43, 1963) described marked shortening of the duration of postoperative ileus in patients using neural electric gastric stimulation ("NEGS") with a single antral intraluminal electrode and a single cutaneous reference electrode. However, subsequent well-controlled studies have failed to confirm a significant effect of NEGS on antral contractions or postoperative ileus.

Later studies have focused upon Electrical Control Activity ("ECA") entrainment, termed Gastric Electrical Pacing by Sarna et. al., 1976. Distal antral stimulation in dogs produced a delay in emptying of liquids and solids. Proximal stimulation to entrain ECA to a higher frequency was found to have no effect on antral emptying. These findings were confirmed by Kelly K A, and Code C F "Duodenal-gastric reflux and slowed gastric emptying by electrical pacing of the canine duodenal pacesetter potential" *Gastroenterol.,* 72:429, 1977. Kelly et. al., 1977 demonstrated retrograde propulsion of duodenal contents with distal duodenal stimulation and entrainment of the duodenal pacesetter potential.

J. C. Eagon et. al., 1995 studied carefully the effects of low-frequency (0–20 Hz) electrical stimulation on canine gastric electrical activity (GEA), motility and emptying and concluded that although an increment of GEA frequency was observed when stimulating at 6 and 30 cycles-per-minute (cpm), gastric contractions and emptying were not affected by stimulation in the low frequency range. More optimistic findings were reported by The GEMS Study Group, 1996 in improvement of nausea and vomiting in humans, but no dramatic change in gastric emptying was evident.

Chen et al., October 1995, described slight acceleration of gastric emptying in a pilot study of a small number of patients with gastroparesis by performing GEP at one site on the greater curvature of the stomach and entraining ECA to a frequency 10% higher than the electrophysiological or basal. However, Bellahsene et. al., 1992, in a canine model of gastroparesis, failed to show any effect from GEP.

The within invention specifically utilizes a mathematical or computer model of gastric stimulation in order to derive the parameters of the electrical stimuli required to produce artificially propagated contractions in the stomach.

Mirrizzi et. al., 1985 (Mirrizzi N., R. Stella, U. Scafoglieri "A model of extra cellular wave shape of the gastric electrical activity" *Med. Biol. Eng. & Comput,* 23:33–37, 1985) and Mirrizzi et. al., 1986 (Mirrizzi N., R. Stella, U. Scafoglieri "Model to stimulate the gastric electrical control activity on the stomach wall and on abdominal surface" *Med. Biol. Eng. & Comput,* 24:157–163, 1986) suggest a conical dipole model of gastric electrical activity. The gastric electrical field was considered to be a result of electrical dipoles pointing towards the centre of the stomach in an approximately 2 mm. wide ring of depolarized smooth muscle cells. The conical dipole model assumes that the first such ring originates in the mid-corpus. With the continuous repolarization of the proximal layer of cells in the ring and the depolarization of the distal layer, the ring can be thought of as a dynamic entity that moves with an increasing velocity towards the pylorus, thus representing the dynamics of the depolarization-repolarization phenomena that take place in a healthy stomach.

However, a recent study by the inventors of the within invention (Mintchev, M. P. and K. L. Bowes "Conoidal Dipole Model of the Electrical Field Produced by the Human Stomach" *Med. Biol. Eng. & Comput.* 33:179–85, 1995) suggested a conoidal dipole model of gastric electric field (the "conoidal model") as an improvement over the previously known conical dipole model. In the conoidal model, as described in detail in Mintchev et. al., 1995, the area S of a d-wide ring of depolarized cells represented as dipoles pointing toward the center was given with:

$$S=2\pi\delta r(t) \qquad \text{Equation [1]}$$

where r(t) represented the radii of the circles that build up this ring of dipoles. On the other hand, the relationship between the vector of the dipole density D and the vector of the equivalent dipole moment P (which is directly related to the number of depolarized cells in the ring and their depolarization level) is given with:

$$D=P/S \qquad \text{Equation [2]}$$

The articles by Mirrizzi et al., 1985 and 1986, set out above, suggested that |P| could be considered constant and estimated its value to be $2.2 \times 10^{-6}$ C.m. They assumed that the charge distribution on each side of a given polarized cell in the ring is approximately equal, and the number or polarized cells in the ring remains the same, while the density of the cells increases in distal direction with the decrement of S. When considering gastric stimulation in the conoidal model, this assumption is deviated from and |P| is considered to be a variable. In fact, it is believed, and the conoidal model assumes, that changes in gastric electrical activity (GEA) associated with contractions cause the amplitude of this vector to fluctuate. However, these fluctuations could very well be obscured when the vector distance r between the point of interest and the infinitesimal area segment dS located on the ring of depolarized cells is sufficiently great (e.g. in electrogastrography):

$$V_Q = [1/4\pi\varepsilon] \int_{(g)} [D \cdot \rho/|\rho|^3] dS \qquad \text{Equation [3]}$$

Although the conoidal model and equation [3] relate to the spontaneous GEA of a normal stomach (as is discussed further below), it is believed that the conoidal model may be able to reconstruct the temporal and propagation organization of the missing contractions in a gastroparetic stomach.

There is therefore a need for a method and a device for the electrical stimulation of smooth muscle comprising a portion of the gastrointestinal tract in order to facilitate or aid at least a partial emptying of such portion. Further, there is a need for a method and a device for the electrical stimulation of the smooth muscle of the stomach. Finally, there is a need for a method and a device which utilize the conoidal model to derive the parameters of the electrical stimulus required to produce artificially propagated contractions in the stomach sufficient to facilitate at least a partial emptying of the stomach.

SUMMARY OF THE INVENTION

This invention relates to a device for electrical stimulation of smooth muscle comprising a portion of the gastro-intestinal tract, a method for using the device of the within invention and a method for electrical stimulation of the smooth muscle. In particular, the device and the methods relate to the electrical stimulation of the smooth muscle in a manner such that local contractions of the portion of the gastrointestinal tract are artificially propagated therethrough in order to facilitate or aid at least a partial emptying of such portion. Preferably, the local contractions are artificially propagated by phase locking or time shifting the electrical stimulus, which is applied to the smooth muscle circumferentially about the portion at two or more locations.

Preferably, when stimulating the smooth muscle of the stomach, the within invention utilizes the conoidal mathematical or computer model of gastric stimulation in order to derive the parameters of the electrical stimuli required to produce artificially propagated contractions in the stomach. Further, the conoidal model is preferably used to calculate the positions or locations for application of the electrical stimuli in the stomach, to determine the configurations of circumferential electrode sets utilized by the device of the within invention to produce the local circumferential contractions of the stomach and to determine the exact time delays between the applied phase-locked electrical stimuli in order to recreate a distally moving peristalsis.

In the preferred embodiment, the within invention is directed at a method and a device for simulating gastric electrical stimulation using the conoidal model of gastric electrical activity. Thus, the invention may suggest a possible avenue toward reliable gastric pacing. Further, the invention implements the concept of artificially propagated contractions by phase-locking or time-shifting local non-propagated contractions produced by electrical stimuli applied at selected locations in the stomach, by circumferential electrode sets of the within invention. As described above, the temporal and propagation organization of gastric electrical activity described in the conoidal model is used to derive the geometry of the stimulating electrode sets and the time shifts for phase-locking of the electrical stimuli applied to the different circumferential electrode sets.

In a first aspect of the invention, the invention is directed at a device for electrical stimulation of smooth muscle comprising a portion of the gastro-intestinal tract, wherein the portion of the gastro-intestinal tract defines a longitudinal axis extending therethrough. The device is comprised of:

(a) a proximal electrode set for arrangement circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) at least one distal electrode set for arrangement circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) at least one power source for providing an electrical stimulus to the proximal and distal electrode sets sufficient to stimulate the smooth muscle to produce the local circumferential contractions;

(d) a timing mechanism, associated with the power source, for phase locking the electrical stimulus such that the electrical stimulus is applied to the proximal and distal electrode sets successively and repetitively;

wherein the axially spaced relationship between the electrode sets and the timing of the electrical stimulus applied to the electrode sets are selected such that the local circumferential contractions are artificially propagated distally through the portion of the gastro-intestinal tract.

In a second aspect of the invention, the invention is directed at a method for electrical stimulation of smooth muscle comprising a portion of the gastro-intestinal tract, wherein the portion of the gastro-intestinal tract defines a longitudinal axis extending therethrough and wherein the method is performed using a device comprised of a proximal electrode set and at least one distal electrode set. The method is comprised of the steps of:

(a) arranging the proximal electrode set circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) arranging each of the distal electrode sets circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) applying an electrical stimulus to the proximal and distal electrode sets sufficient to stimulate the smooth muscle to produce the local circumferential contractions, wherein the electrical stimulus is phase-locked such that the electrical stimulus is applied to the proximal and distal electrode sets successively and repetitively;

wherein the axially spaced relationship between the electrode sets and the timing of the phase-locking of the electrical stimulus applied to the electrode sets are selected such that the local circumferential contractions are artificially propagated distally through the portion of the gastro-intestinal tract.

In a third aspect of the invention, the invention is directed at a method for electrical stimulation of smooth muscle comprising a portion of the gastro-intestinal tract, wherein the portion of the gastro-intestinal tract defines a longitudinal axis extending therethrough. The method is comprised of the steps of:

(a) applying an electrical stimulus at a proximal location to the smooth muscle circumferentially about the portion of the gastro-intestinal tract in a plane substantially perpendicular to the longitudinal axis, wherein the electrical stimulus is sufficient to stimulate the smooth muscle to produce a local circumferential contraction at the proximal location;

(b) applying an electrical stimulus at at least one distal location to the smooth muscle circumferentially about the portion of the gastro-intestinal tract in a plane substantially perpendicular to the longitudinal axis, wherein the distal location is in axially spaced relationship relative to the proximal location and wherein the electrical stimulus is sufficient to stimulate the smooth muscle to produce a local circumferential contraction at the distal location; and (c) phase-locking the electrical stimulus applied at the proximal and distal locations such that the electrical stimulus is applied at the proximal and distal locations successively and repetitively;

wherein the axially spaced relationship between the proximal and distal locations and the timing of the phase-locking of the electrical stimulus applied to the locations are selected such that the local circumferential contractions are artificially propagated distally through the portion of the gastro-intestinal tract.

In the first, second and third aspects of the invention, the portion of the gastro-intestinal tract may be comprised of the esophagus, the stomach, the small intestine, the large intestine, the anal sphincter and combinations thereof. However, in the preferred embodiment, the portion of the gastro-intestinal tract is comprised of the stomach. Further, in all aspects of the invention, the artificial propagation of local contractions through the gastro-intestinal tract, and in particular the stomach, is preferably sufficient to facilitate at least a partial emptying thereof.

The electrical stimulus may be applied at any location which permits the electrical stimulus to produce a local contraction at the desired portion of the gastro-intestinal tract. Thus, the electrode sets of the device may be affixed, applied or implanted at any such location. However, preferably, the electrical stimulus is applied at a location in communication with, or within, the layers comprising the wall of the gastro-intestinal tract. In the preferred embodiment, the electrical stimulus is applied subserosally. Thus, the electrode sets of the device are preferably implanted subserosally in the gastro-intestinal tract.

Further, in the third aspect of the invention, the electrical stimulus is preferably applied at at least two distal locations, and more preferably, at at least three distal locations. The number of distal locations will be determined by, amongst other factors, the size or dimensions, and in particular the length, of the portion of the gastro-intestinal tract to be stimulated and by the desired parameters and effectiveness of the artificially propagated local circumferential contractions. In the preferred embodiment, the electrical stimulus is applied at three distal locations.

Similarly, in the first and second aspects of the invention, the device is preferably comprised of at least two distal electrode sets, and more preferably, at least three distal electrode sets. The number of distal electrode sets will similarly be determined by, amongst other factors, the size or dimensions, and in particular the length, of the portion of the gastro-intestinal tract to be stimulated and by the desired parameters and effectiveness of the artificially propagated local circumferential contractions. In the preferred embodiment, the device is comprised of three distal electrode sets.

In the preferred embodiment, the proximal location is located in about the mid-corpus of the stomach. The distal locations are located distally to the proximal location and in an axially spaced relationship with each other such that the phase-locking of the electrical stimulus produces a local circumferential contraction at the proximal location and each distal location in succession. Similarly, the proximal electrode set is located in about the mid-corpus of the stomach. The distal electrode sets are located distally to the proximal electrode set and in an axially spaced relationship with each other such that the phase-locked electrical stimulus produces a local circumferential contraction at the proximal electrode set and each distal electrode set in succession.

As well, in the first and second aspects of the invention, each of the proximal and distal electrode sets of the device is comprised of at least one active electrode and at least one ground electrode. Preferably, the active electrodes are connected to the power source, and the electrical stimulus is applied to the active electrodes, in a manner such that the electrical stimulus is provided concurrently to each of the active electrodes included in an electrode set.

In the preferred embodiment, each active electrode is paired with a ground electrode. However, the active electrodes may share one or more ground electrodes. For example, the electrode set may be comprised of a single ground electrode and one or more active electrodes. Thus, in the preferred embodiment, the number of active electrodes is greater than or equal to the number of ground electrodes in each of the proximal and distal electrode sets.

The electrodes of each electrode set may be spaced apart circumferentially about the portion of the gastro-intestinal tract at any distance permitting the electrical stimulus to produce a local circumferential contraction. However, in the preferred embodiment, the distance between the electrodes in each of the proximal and distal electrode sets is between about 2 to 4 centimeters. Thus, the specific number of electrodes comprising an electrode set will be dependent upon the specific circumference of the portion of the gastro-intestinal tract at the location of the electrode set.

Although the electrical stimulus applied at the proximal and distal locations, and to the proximal and distal electrodes, may be either direct or alternating, the electrical stimulus is preferably alternating. Thus, in the first aspect of the invention regarding the device, the electrical stimulus is preferably provided by an alternating current source.

Further, although the alternating electrical stimulus may be either monopolar or bipolar, the alternating electrical stimulus is preferably bipolar. Thus, the alternating current source of the device is preferably a bipolar alternating current source.

Finally, the alternating electrical stimulus may have any shape suitable for producing the local circumferential contractions. However, the shape of the alternating electrical stimulus is preferably rectangular or square. Thus, the alternating current source is preferably a rectangular alternating current source or a square alternating current source.

The frequency of the alternating current source, in the first aspect of the invention, and the frequency of the alternating electrical stimulus, in the second and third aspects of the invention, is preferably between about 5 to 500 Hertz, and more preferably, is between about 5 to 50 Hertz. In the preferred embodiment, the frequency is about 50 Hertz.

The voltage of the alternating current source, in the first aspect of the invention, and the voltage of the alternating electrical stimulus, in the second and third aspects of the invention, is preferably less than or equal to about 20 Volts, peak to peak, and more preferably, is between about 10 to 20 Volts, peak to peak. In the preferred embodiment, the voltage is between about 14 to 15 Volts, peak to peak.

However, the voltage and frequency of the alternating current source, in the first aspect of the invention, and the voltage and frequency of the alternating electrical stimulus, in the second and third aspects of the invention, may be any voltage and frequency sufficient to produce the local circumferential contractions without causing any significant damage to the tissues of the gastro-intestinal tract.

Finally, in the third aspect of the invention, the electrical stimulus is phase-locked such that the electrical stimulus is applied to the location for a selected interval, following which there is an interval of no stimulation before the application of the electrical stimulus to the next successive location. Preferably the interval of no stimulation is equivalent to the interval of stimulation. Further, the interval and the equivalent interval are selected to provide a period of time sufficient to permit the electrical stimulus to produce the local circumferential contractions and to permit the artificial propagation of the contractions through the portion of the gastro-intestinal tract, preferably in a manner facilitating at least a partial emptying thereof. In the preferred embodiment, the electrical stimulus is applied to the location for an interval of between about 2 to 4 seconds, following which there is an equivalent interval of no stimulation before the application of the electrical stimulus to the next successive location.

In the second aspect of the invention, the phase-locked electrical stimulus, as described above, is applied to the electrode set. Thus, in the preferred embodiment, the electrical stimulus is applied to the electrode set for an interval of between about 2 to 4 seconds, following which there is an equivalent interval of no stimulation before the application of the electrical stimulus to the next successive electrode set. In the first aspect of the invention, the timing mechanism applies the phase-locked electrical stimulus in this manner.

BRIEF DESCRIPTION OF DRAWINGS

Embodiments of the invention will be described with reference to the accompanying tables and drawings, in which:

FIG. 8 is a table showing the effect of the application of the electrical stimuli, as shown in FIGS. 6 and 7, on the gastric emptying of 200 ml of water;

DETAILED DESCRIPTION OF THE INVENTION

Figure 1:
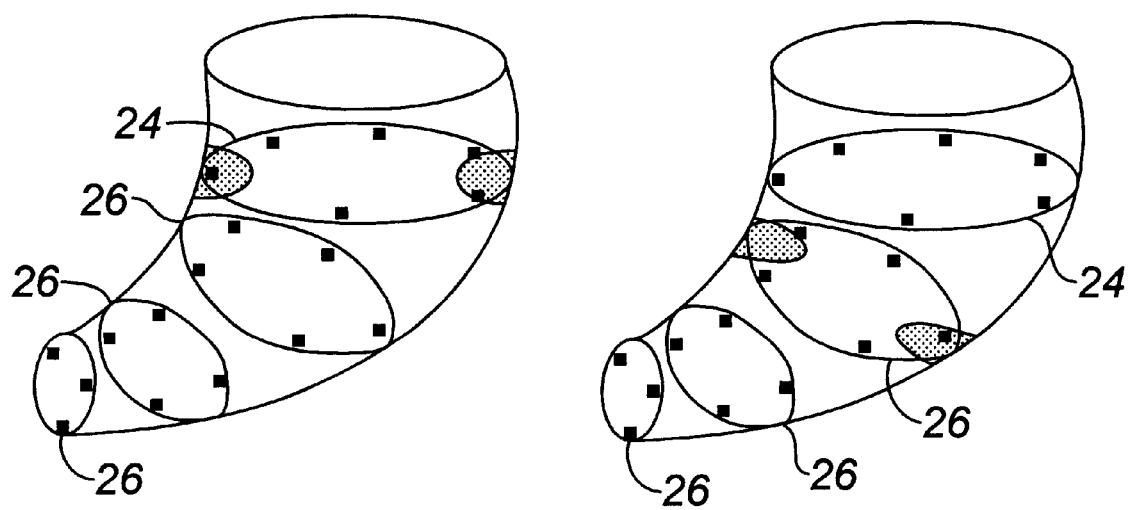
FIG. 1 shows a simulated pacing session produced by the model of the within invention in a first study conducted by the inventors.
Figure 1:
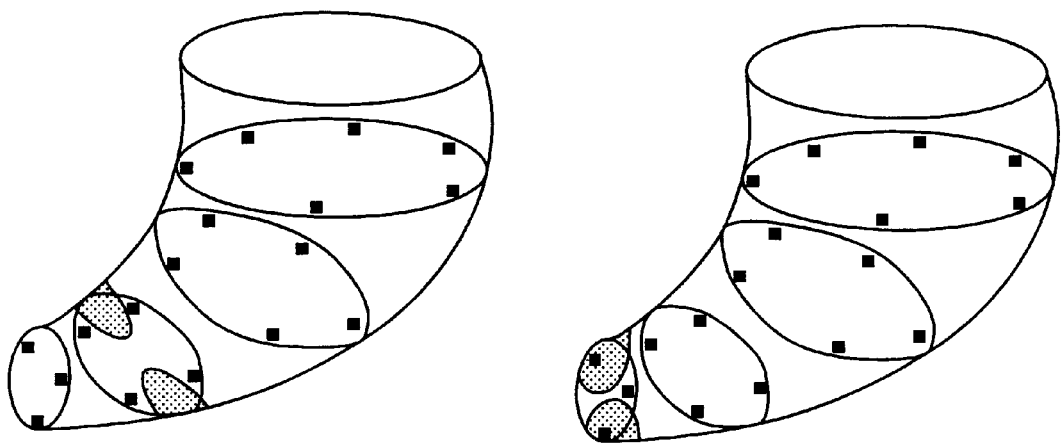

This invention relates to a device (20) for electrical stimulation of smooth muscle comprising a portion of the gastro-intestinal tract, a method for using the device (20) of the within invention and a method for electrical stimulation of the smooth muscle. In the preferred embodiment, the device (20) and the methods relate to the electrical stimulation of the smooth muscle in a manner such that local contractions of the portion of the gastro-intestinal tract are artificially propagated distally therethrough in order to facilitate or aid at least a partial emptying of such portion. The local contractions are artificially propagated by phase locking or time shifting the electrical stimulus, which is applied to the smooth muscle circumferentially about the portion at two or more locations.

The portion of the gastro-intestinal tract may be comprised of the esophagus, the stomach, the small intestine, the large intestine, the anal sphincter and combinations thereof. However, in the preferred embodiment, the portion of the gastro-intestinal tract is comprised of the stomach. Further, the portion of the gastro-intestinal tract defines a longitudinal axis extending therethrough. In the stomach, the longitudinal axis is centrally or equidistantly located between the greater and lesser curvatures of the stomach.

The electrical stimulus may be applied at any location in the body of the patient or the gastro-intestinal system of the patient which permits the electrical stimulus to produce a local contraction at the desired portion of the gastro-intestinal tract. However, preferably, the electrical stimulus is applied at a location in communication with, or within, the layers comprising the wall of the gastro-intestinal tract. In the preferred embodiment, the electrical stimulus is applied subserosally.

The invention provides electrical stimulation to the smooth muscle of the selected portion of the gastro-intestinal tract, which smooth muscle is preferably comprised of innervated muscle tissue. Although the muscle tissue itself may be directly stimulated, in the preferred embodiment, as discussed further below, it is theorized that the smooth muscle is neurally electrically stimulated through the nerves associated with and innervating the muscle tissue in order to produce the contraction of the smooth muscle. Thus, in the preferred embodiment, the invention is used in patients with intact local gastric nerves. The invention may not be useful in patients with impaired local gastric nerves.

Further, as stated above, when stimulating the smooth muscle of the stomach, the within invention attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the gastro-intestinal tract in a plane substantially perpendicular to the longitudinal axis of the portion. The electrical stimulus is applied at a proximal location and at at least one distal location. The distal location is in axially spaced relationship relative to the proximal location. Further, the applied electrical stimulus is selected to be sufficient to stimulate the smooth muscle to produce the local circumferential contractions at the proximal and distal locations.

In the device (20) of the within invention, the device (20) is comprised of a proximal electrode set (24) and at least one distal electrode set (26). The proximal electrode set is arranged circumferentially at the proximal location, while the distal electrode set (26) is arranged at the distal location. The proximal and distal electrode sets (24, 26) are arranged circumferentially in the plane substantially perpendicular to the longitudinal axis of the portion of the gastro-intestinal tract. Further, the electrode sets (24, 26) are provided with an electrical stimulus sufficient to stimulate the smooth muscle to produce the local circumferential contractions at the locations of the electrode sets (24, 26) by at least one power source (22).

Further, the electrical stimulus stimulating the smooth muscle is phase-locked such that the electrical stimulus is applied at the proximal and distal locations successively and repetitively. In the device (20), the device (20) is further comprised of a timing mechanism (28) associated with the power source (22) for phase locking the electrical stimulus such that the electrical stimulus is applied to the proximal and distal electrode sets (24, 26) successively and repetitively. The axially spaced relationship between the proximal and distal locations, or the proximal and distal electrode sets (24, 26) of the device (20), and the timing of the phase-locking of the electrical stimulus are selected such that the local circumferential contractions are artificially propagated distally through the portion of the gastro-intestinal tract. In the preferred embodiment, the conoidal mathematical or computer model of gastric stimulation is used to derive the specific parameters of the electrical stimuli required to produce the artificially propagated contractions.

Spontaneous mechanical activity of the portion of the gastro-intestinal tract, such as the stomach in the preferred embodiment, could interfere negatively with the artificially invoked and propagated local contractions. Therefore, in the preferred embodiment, the within invention is used in circumstances of gastroparesis or abnormally delayed gastric emptying.

As stated, the within invention is based upon the conoidal dipole model of gastric electrical activity, as described earlier, and implies that artificially propagated gastric contractions can be produced by circumferential stimulation of the smooth muscle, using circumferential sets of stimulating electrodes (24, 26), and by phase-locking the applied electrical stimulus. The suggested conoidal model is used to derive the geometry of the stimulating electrode sets, the electrode set positions and the actual phase-locking of the stimulating electrical stimulus. Of course, the model has the limitations of any mathematical approximation of a real-life physiological phenomenon. However, it is believed that most of the assumptions made in this model are relevant to the electrophysiology of the human stomach. This is supported by the test data set out below.

However, producing artificially propagated contractions does not necessarily mean that an adequate gastric emptying would be obtained, nor does it mean that the set of stimulating electrodes used in this model should not be modified as real-life experiments on humans indicate. Preferably, however, the artificial propagation of the local contractions through the portion of the gastro-intestinal tract, such as the stomach, is sufficient to facilitate at least a partial emptying thereof. Thus, the artificially contracting stomach may need to be synchronized with any spontaneous contractions of the duodenum or opening of the pylorus. The potential requirement for synchronization may be addressed by utilizing biofeedback from the duodenum to control gastric electrical stimulation. Further, if the proximal duodenum or pylorus are mechanically inactive, the implantation of electrodes on the pylorus or duodenum may be required, which are stimulated in synchronization with the electrodes in the stomach. However, it is possible that the duodenum may regulate itself based upon the artificial gastric contractions.

With respect to the mathematical model, as stated, the conoidal dipole model and equation [3] relate to the spontaneous gastric electrical activity of a normal stomach. Therefore, it is theorized that the following possible problems may arise which are related to the eventual abnormalities associated with the occurrence and propagation of the depolarization ring. Note that these abnormalities tend to be strongly related to abnormal gastric function:

(a) The ring of depolarized cells in a dysfunctional stomach may not have the same characteristics as the ring of depolarized cells observed in healthy subjects;

(b) The propagation of the ring in a distal direction may be disturbed; and (c) More than one depolarization ring may exist at the same time on the stomach wall.

Potential problem (a) simply indicates that the vector P in the conoidal dipole model of a dysfunctional stomach may not have the same value and possibly the same direction as the P-vector associated with normal stomachs. The second potential problem (b) implies that the mathematical expression describing the propagation of the ring in the conoidal model may not be completely accurate and may require substitution with a refined model which defines the new pathological behavior of the stomach, as such pathologies become known and understood. The third potential problem (c) is related to the phenomenon of gastric electrical uncoupling and indicates that the stomach can be split into several different areas. In each of these areas there may be a separate ring of depolarized cells that has its own vector P and law of propagation.

Stimulation might be required when each of the above problems exists separately or any combination of these problems is present. However, it is difficult, if not impossible, to separate quantitatively the problems and determine their relative significance in a given pathological situation. However, it may be assumed that in most cases, a stomach that would need pacing would be gastroparetic, i.e., its spontaneous mechanical activity would be minimal, or nonexistent. Therefore, in the preferred embodiment, the within invention is used in circumstances of gastroparesis or abnormally delayed gastric emptying.

As stated, it is well known that gastric contractions are controlled by GEA. Moreover, the temporal and propagation organization of these contractions is strongly related to the organization of GEA. Therefore, according to the within invention, the temporal and propagation organization of the missing contractions are attempted to be reconstructed in a gastroparetic stomach using the existing conoidal model of gastric electric field, thus deriving a computer model of gastric electrical stimulation. The conoidal model may be used to calculate the positions and determine the configurations of the circumferential electrode sets needed to produce the local circumferential contractions and to determine the delays between the phase-locked stimuli, including the interval of stimulation and the interval of no stimulation, applied to these electrode sets so that a distally moving peristalsis is recreated.

Ideally, in order to facilitate a partial or complete emptying of a gastroparetic stomach, it is preferable to recreate the temporal and propagation organization of gastric contractions common for the average healthy people. The within invention does this by invoking local circumferential contractions and artificially propagating them distally towards the pylorus. The primary issues which are preferably addressed to accomplish this purpose are: (1) the geometry of the stimulating electrodes that may be used to produce the local circumferential contraction; (2) the frequency and the duration of the electrical stimulus that may produce such contraction; and (3) the manner in which the applied electrical stimulus may be phase-locked so that local circumferential contractions may be propagated from one electrode set to the next.

In order to address and determine the above three points, the following assumptions have been made with respect to the conoidal model of the within invention:

(a) regardless of whether the simulated stomach (a truncated conoid in a spherical system of coordinates) is able to produce an adequate ring of depolarized cells or not, and regardless of whether and how this ring moves distally, there are preferably no contractions taking place in the stomach, i.e. there is preferably a complete gastroparesis and the organization and propagation of gastric contractions need to be recreated;

(b) the local contraction produced between the active and the ground electrode of a given electrode pair would displace the stomach wall towards the longitudinal axis of the stomach by approximately 1–3 cm (depending on the amplitude of the stimulus) and would not propagate distally;

(c) phasic contractions take place simultaneously in circumferential planes (Mintchev et. al., 1995; Mirrizzi et. al., 1985; and Mirrizzi et. al., 1986.);

(d) phasic contractions propagate with an increasing velocity towards the pylorus and have well-known temporal organization (Mintchev et. al. 1995; Mirrizzi et. al. 1985; and Mirrizzi et. al. 1986)

(e) only one circumferential contraction is present in the stomach at any given moment;

(f) only antral contractions are important from a mechanical point of view.

Further, in the conoidal computer model of the within invention, it is assumed that the velocity of propagation (in cm/s) of the depolarization wave along the longitudinal axis of the stomach of an average human can be expressed with:

$$v(t)=0.00825-0.00575[(\exp(-0.362t)], \quad \text{Equation [1]}$$

where t=0, 1, 2 . . . 19 represents the discrete time (in seconds) for which the depolarized ring propagates from its origin in the mid corpus to the pylorus. The model considers the differences in the velocities of propagation along the greater and lesser curvatures as well. In order to incorporate these concepts into the stimulation modeling, the following additional assumptions have been made:

(a) the propagation of the band of depolarization takes place from the mid corpus (second No. 0) towards the pylorus (second No. 19) with an increasing and known velocity;

(b) the time is discrete from 0 (the origin of the depolarization wave in the mid corpus) to 19 (distal pylorus) seconds, with a step of 1 second;

(c) the first proximal set of stimulating electrodes (24) is placed in the proximal antrum at a position reached by the propagating depolarization band (described in the original conoidal model) at second No. 7;

(d) each subsequent distal set of simulating electrodes (26) is located at a position corresponding to about a 4 to 8-second shift with respect to the previous electrode set (24, 26).

The exact distance of the circumferential electrode sets (24, 26) from the initial position of the depolarization ring in the mid corpus can be estimated from the exponential equation [4] for the velocity of propagation in an average human stomach:

$$l = \sum_t \{[v(t) + v(t+1)]/2\} \cdot T; \quad t = 0, 1, 2 \ldots T_e - 1, \quad \text{Equation [5]}$$

where $T_e$ is the second associated with the given electrode position and T=1 s.

The circumference of a given circle on which an electrode set (24, 26) is positioned is determined by the radius of that circle. This radius, which could be regarded as a function of the discrete time, is calculated using previously described technique (Mintchev et. al., 1995). The number of electrodes in a given set (24, 26) may be calculated easily knowing the circumference and assuming that the interelectrode distance is between about 2 and 4 cm in the preferred embodiment of the invention.

In the preferred embodiment, each of the proximal and distal electrode sets (24, 26) of the device (20) is comprised of at least one active electrode (30) and at least one ground electrode (32). Preferably, the active electrodes (30) are connected to the power source, and the electrical stimulus is applied to the active electrodes (30), in a manner such that the electrical stimulus is provided concurrently to each of the active electrodes (30) included in an electrode set (24, 26).

Further, in the preferred embodiment, each active electrode (30) is paired with a ground electrode (32) to define an electrode pair. However, the active electrodes (30) may share one or more ground electrodes (32). For example, the electrode set (24, 26) may be comprised of a single ground electrode (32) and one or more active electrodes (30). Thus, in the preferred embodiment, the number of active electrodes (30) is greater than or equal to the number of ground electrodes (32) in each of the proximal and distal electrode sets (24, 26). The number of electrode pairs will therefore be determined by the number of active (30) electrodes.

The electrodes (30, 32) of each electrode set (24, 26) may be spaced apart circumferentially about the stomach or other portion of the gastro-intestinal tract at any distance permitting the electrical stimulus to produce a local circumferential contraction. However, as stated, in the preferred embodiment, the distance between the electrodes (30, 32) in each of the proximal and distal electrode sets (24, 26) is between about 2 to 4 centimeters. Thus, as stated, the specific number of electrodes (30, 32) comprising an electrode set (24, 26) will be dependent upon the specific circumference of the portion of the gastro-intestinal tract at the location of the electrode set (24, 26)

Using these principles and the conoidal model, a net of circumferential stimulating electrodes is built up on the truncated conoid representing the stomach. All active electrodes (30) and all ground or reference electrodes (32) in a given circumferential setup are separately "short-circuited", i.e. the active electrodes (30) simultaneously delivered one and the same electrical stimulus, while the ground electrodes (32) are attached to one and the same ground.

The electrical stimulus is preferably applied at at least two distal locations, and more preferably, at at least three distal locations. The number of distal locations will be determined by, amongst other factors, the size or dimensions, and in particular the length, of the portion of the gastro-intestinal tract to be stimulated and by the desired parameters and effectiveness of the artificially propagated local circumferential contractions. In the preferred embodiment, the electrical stimulus is applied at three distal locations. Thus, the device is also preferably comprised of at least two distal electrode sets (26), and more preferably, at least three distal electrode sets (26). In the preferred embodiment, the device (20) is comprised of three distal electrode sets (26).

As indicated, in the preferred embodiment, the proximal location, and thus the location of the proximal electrode set (24), is in about the mid-corpus of the stomach. The distal locations, and thus the locations of the three distal electrode sets (26), are distal to the proximal location, or proximal electrode set (24), and in an axially spaced relationship with each other such that the phase-locking of the electrical stimulus produces a local circumferential contraction at the locations in succession.

Using the conoidal model for the application of these principles to an average normal stomach, the proximal and three distal electrode sets (24, 26) preferably have 6, 5, 4 and 3 electrodes respectively. The proximal electrode set (24) comprising 6 electrodes is positioned 5.1 cm distally from the mid-corpus. Table 1, as set out below, shows the distances between the circumferential electrode sets (24, 26) calculated from the central line between the greater and the lesser curvatures or along the longitudinal axis of the stomach. These distances were calculated using equations [4] and [5]. In an actual setup, the arrangement of the electrode sets (24, 26) preferably starts from the most distal set (Electrode Set No. 4, the closest to the pylorus), since the area of the mid-corpus is not very clearly defined anatomically.

TABLE 1

Distances between different circumferential electrode sets estimated on the central line between the greater and the lesser curvatures on the anterior gastric wall, based upon the conoidal model

| | Mid-Corpus - Electrode Set 1 | Electrode Set 1 - Electrode Set 2 | Electrode Set 2 - Electrode Set 3 | Electrode Set 3 - Electrode Set 4 |
|---|---|---|---|---|
| Distances (cm) | 5.1 | 3.23 | 3.29 | 3.36 |

The circumference of the proximal location, or the most proximal circle of the gastric conoid on which the proximal electrode set (24) was placed, was found to be 19.48 cm. Accordingly, the six stimulating electrodes were positioned 3.24 cm apart. Table 2, as set out below, shows the number of stimulating electrodes (30) and the interelectrode distances in each of the four stimulating electrode sets (24, 26).

TABLE 2

Number of electrodes in a given circumferential electrode set and the distances between the individual electrodes in the set, based upon the conoidal model

| | Electrode Set 1 (most proximal) | Electrode Set 2 | Electrode Set 3 | Electrode Set 4 (most distal) |
|---|---|---|---|---|
| Number of Electrodes | 6 | 5 | 4 | 3 |
| Inter-electrode Distance (cm) | 3.24 | 3.45 | 3.41 | 2.93 |

Figure 2:
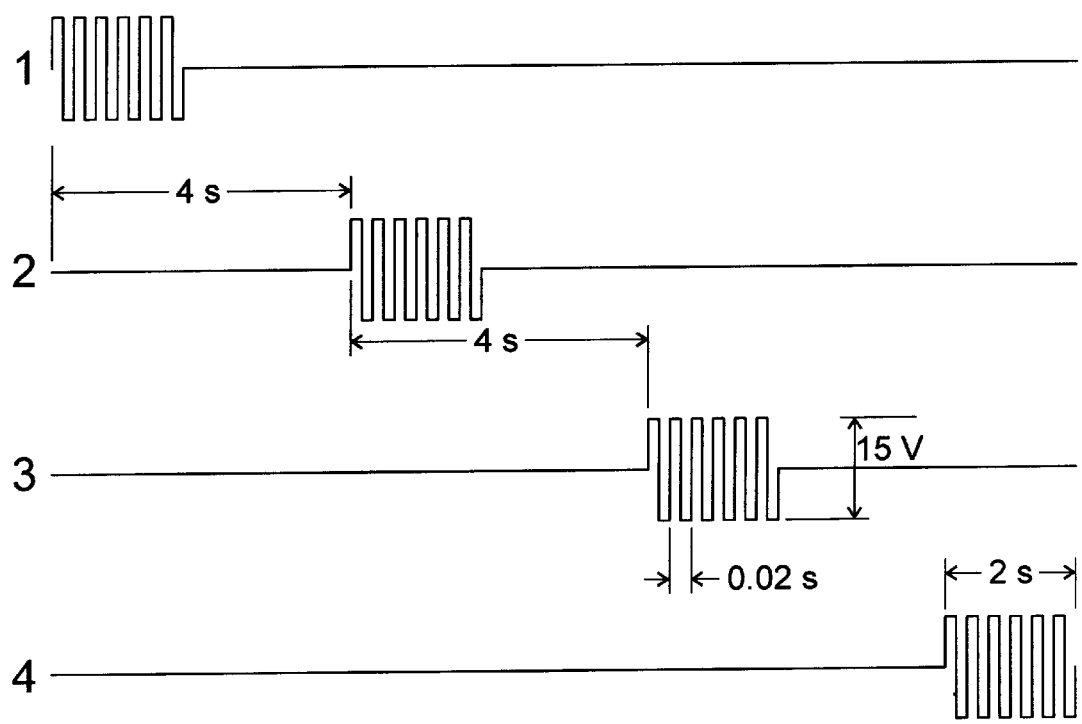
FIG. 2 shows the phase-locking of the electrical stimuli which produced the contractions shown in FIG. 1.

FIG. 1 shows a simulated pacing session produced by the model. The phase-locking of the electrical stimulus that produced the simulated contractions is shown on FIG. 2.

The electrical stimulus applied at the proximal and distal locations, and to the proximal and distal electrodes (24, 26), may be either direct or alternating. However, the electrical stimulus is preferably alternating. Thus, in the device (20), the electrical stimulus is preferably provided by an alternating current source.

Further, the alternating electrical stimulus may be either monopolar or bipolar. However, the alternating electrical stimulus is preferably bipolar. Thus, the alternating current source of the device (20) is preferably a bipolar alternating current source.

As well, the alternating electrical stimulus may have any shape suitable for producing the local circumferential contractions, such as square, rectangular, sinusoidal or sawtooth. However, the shape of the alternating electrical stimulus is preferably rectangular or square. Thus, the alternating current source of the device (20) is preferably a rectangular alternating current source or a square alternating current source.

The frequency of the alternating current source, or the alternating electrical stimulus, is preferably between about 5 to 500 Hertz, and more preferably, is between about 5 to 50 Hertz. In the preferred embodiment, the frequency is about 50 Hertz. The voltage of the alternating current source, or the alternating electrical stimulus, is preferably less than or equal to about 20 Volts, peak to peak, and more preferably, is between about 10 to 20 Volts, peak to peak. In the preferred embodiment, the voltage is between about 14 to 15 Volts, peak to peak.

However, the voltage and frequency of the alternating current source, or the alternating electrical stimulus, may be any voltage and frequency sufficient to produce the local circumferential contractions without causing any significant damage to the tissues of the gastro-intestinal tract. For instance, the studies discussed below suggest that higher and lower voltages and higher and lower frequencies may be used as long as local circumferential contractions are produced and as long as the surrounding stomach tissue is not damaged by the electrical stimuli. In order to avoid damage, it has been found that as the voltage applied to the electrode sets (24, 26) increases, the frequency of the alternating electrical stimulus should also increase. Specifically, the frequency and voltage of the electrical stimulus are chosen in order to obtain relatively strong local contractions without causing any damage to the surrounding tissues.

Finally, the electrical stimulus is phase-locked or time-shifted in order to artificially propagate the contractions distally through the stomach. Phase-locking or time shifting refers to the control of the timing of the applied electrical stimuli in order to result in an artificially propagated "wave" through the stomach. The axially spaced relationship between the proximal and distal locations, or the proximal and distal electrode sets (24, 26), and the timing of the applied electrical stimulus are selected such that the local circumferential contractions are artificially propagated distally through the stomach.

In the preferred embodiment, the electrical stimulus is phase-locked such that the electrical stimulus is applied to the location, or an electrode set, for a selected interval, following which there is an interval of no stimulation before the application of the electrical stimulus to the next successive location or electrode set. Preferably the interval of no stimulation is equivalent to the interval of stimulation, however, this may vary. Further, the interval and the equivalent interval are selected to provide a period of time sufficient to permit the electrical stimulus to produce the local circumferential contractions and to permit the artificial propagation of the contractions through the stomach, preferably in a manner facilitating at least a partial emptying thereof.

In the preferred embodiment, the electrical stimulus is applied to the location, or the electrode set, for an interval of between about 2 to 4 seconds, following which there is an equivalent interval of no stimulation before the application of the electrical stimulus to the next successive location or electrode set. Thus, a complete cycle of the application of the electrical stimulus to all of the locations or electrode sets (24, 26) in succession takes from 16 to 32 seconds. However, the length of the interval of stimulation and the length of the interval of no stimulation may be greater or less than the preferred amount as long as a reasonably effective local contraction is artificially propagated through the stomach.

Although the model and the within invention are designed for use with the stomach in the preferred embodiment, as indicated, this invention may also have application to other portions of the gastro-intestinal tract. However, in this case, different electrodes may have to be used due to the thin walls of these tissues.

The within invention is also comprised of a multichannel electrical device (20) that artificially creates and propagates contractions in the gastro-intestinal tract. The device (20) utilizes multi-channel phase-locked stimuli and greater than one set of circumferentially arranged electrodes (24, 26). The device (20) is designed to control the parameters of the electrical stimulus (frequency, voltage, wave pattern or configuration) and the propagation pattern (phase-locking, including the length of the time of the application of the stimuli to the electrode set) depending upon the particular requirements of a particular person. Preferably, the device is an implantable microelectronic unit similar to known cardiac pacemakers. Further, preferably, the device (20) is microprocessor-controlled.

Figure 10:
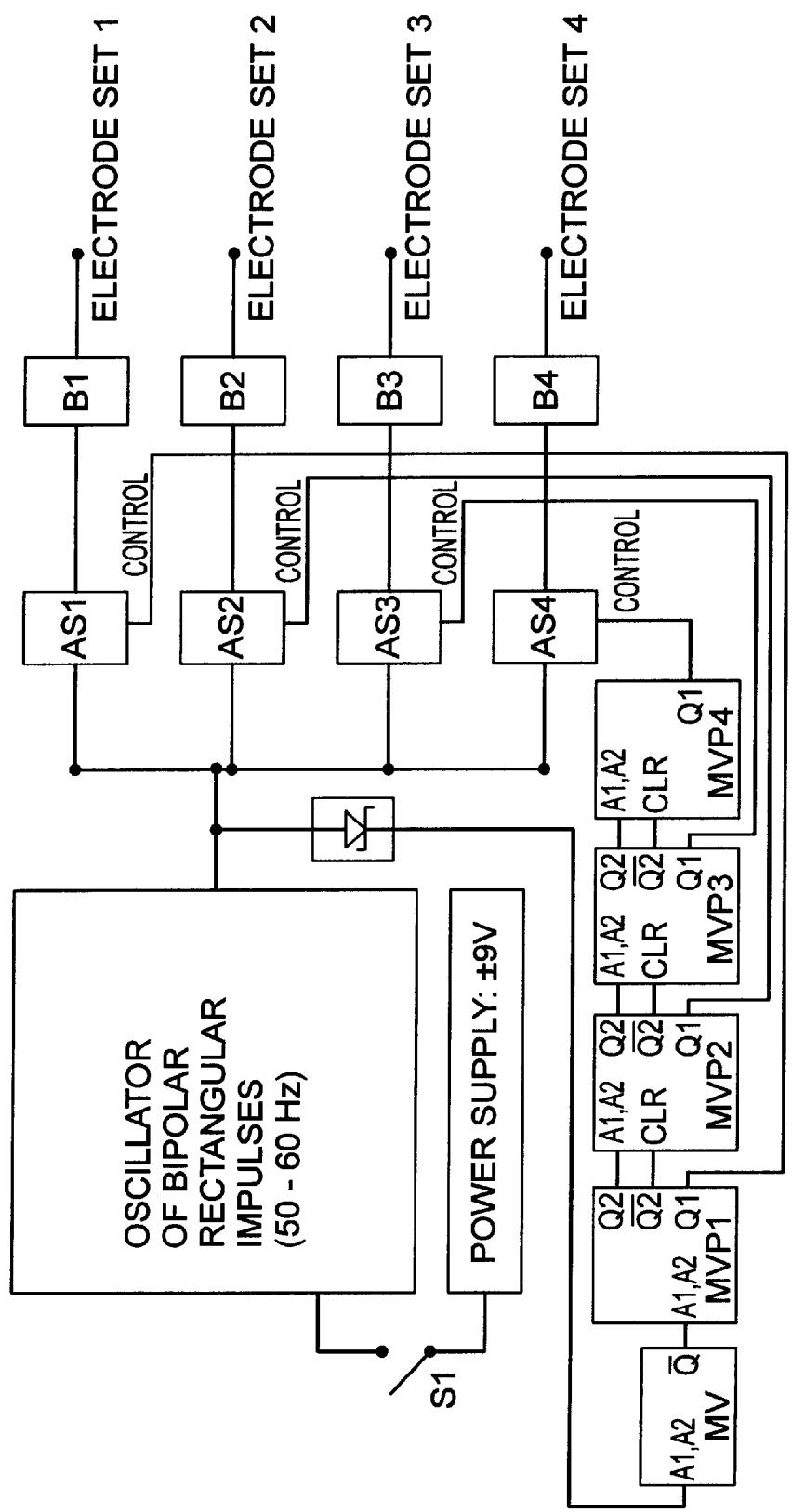
FIG. 10 is a block diagram of the preferred embodiment of a gastric pacemaker.
Figure 11:
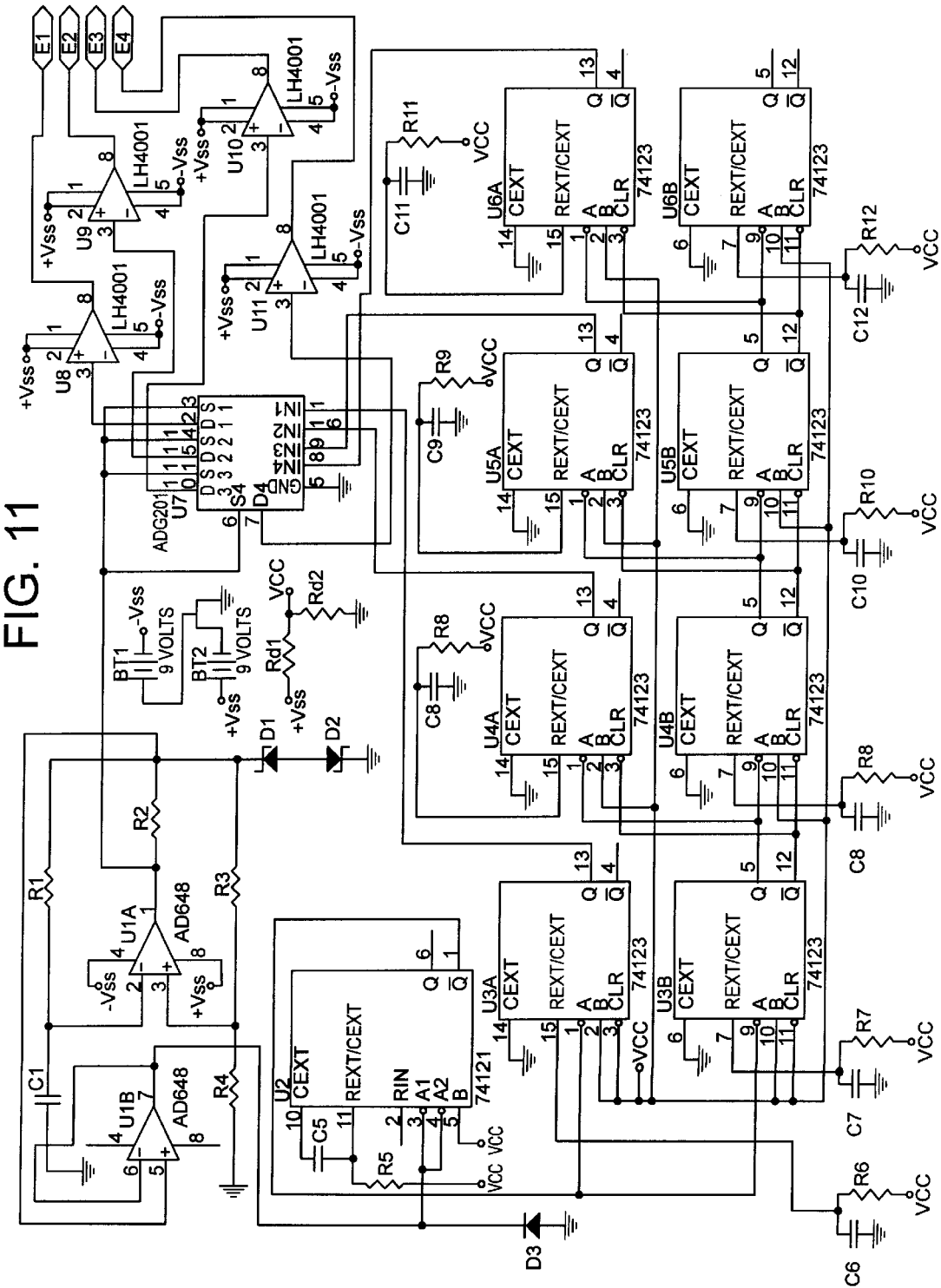
FIG. 11 is a circuit diagram of the gastric pacemaker shown in FIG. 3.

FIGS. 10 and 11 show the preferred embodiment of a gastric pacemaker device (20) for applying the electrical stimuli to produce the artificially propagated contractions in the stomach. In the preferred embodiment, continuous oscillations are produced by a standard electronic oscillator (e.g. astable multivibrator, see IC Op-Amp Cookbook by Walter G. Jung, Howard Sams & Co., Indianapolis, Ind., 1986; ISBN 0-672-224534, pp. 461–465).

The start of the oscillations triggers the first pair (MVP 1) of retriggerable monostable multivibrators (e.g. 74LS123, Texas Instruments, Dallas, Tex.). The first of them produces a 2-second impulse which turns on the switch AS1 (e.g. ADG201A, Analog Devices, Norwood, Mass.) for 2 seconds thus producing the stimulating voltage train or stimulating interval for the first electrode set. At the moment the 2-second impulse for AS1 has started, the inverted output of the second multivibrator initiates a 4-second low-level pulse that is connected to the CLR inputs of the two multivibrators from the second pair, MVP 2, thus blocking both multivibrators from producing any impulses. In the meantime, the first 2-seconds have elapsed, the non-inverting input of the first multivibrator goes back to 0 and the first switch AS1 opens.

Only after the first 4 seconds have elapsed (2 more seconds after the opening of AS1) the first multivibrator from MVP 2, triggered by the first negative slope of the second multivibrator from MVP 1, produces a 2-second impulse which closes the switch AS2 thus producing the stimulating voltage train or stimulating interval for the second electrode set. The second multivibrator from MVP 2 is also triggered by the first negative slope of the second multivibrator from MVP 1 and produces a 4-second pulse. Its inverted output is connected to the CLR inputs of the multivibrators from MVP 3. The negative slope of the non-inverted output of MVP 2 triggers MVP 3 and so on. If there are problems with synchronization, all CLR inputs from all multivibrator pairs could be connected to 5 Volts. This interconnection of the controlling multivibrators allows more than 4 electrode sets to be utilized, if necessary. "B" inputs of all multivibrators are connected to high voltage (5 V, obtained from the +9 V battery using a voltage divider).

The work of MVP 1 is controlled by a single multivibrator MV (e.g. 74LS121, Texas Instruments, Dallas, Tex.), which is programmed to produce impulses with a period of 20 seconds, and its output is connected to the CLR inputs of both multivibrators from MVP 1. The "A" inputs of MV are connected to the conditioned output of the oscillator (conditioned so that the amplitude range of the oscillations at the "A" inputs is 0–5 V using, e.g., appropriate zener diodes, a voltage follower and a diode).

The switch S1 turns the stimulator on/off. At the output, 4 analog buffers (LH4001, National Semiconductor, Crawfordsville, Ind.) are preferably used in order to provide the necessary current (in the range of about 5 mA per electrode set).

Finally, the device (20) of the within invention is preferably microprocessor controlled. For instance, as used in the third study, the device may be controlled by specially-designed software on an IBM 486-33 personal computer.

The application of the within invention and the conoidal model was explored by the inventors in three studies. A first study explored the parameters of the electrical stimulus required to produce a local non-propagated circumferential contraction of the desired portion of the gastro-intestinal tract. A second study explored the phase-locking of the electrical stimulus in order to artificially propagate the local circumferential contractions distally. A third study explored the effect of the application of the phase-locked electrical stimulus on the emptying of the contents of the portion of the gastro-intestinal tract.

In the first study, using two unconscious dogs, two stainless steel wire electrodes (one active, and the other reference or ground) were positioned 3–4 cm apart circumferentially at different locations of the serosal side of the gastric antrum. The electrodes were arranged circumferentially in a plane substantially perpendicular to the longitudinal axis of the stomach. The effect of different stimulating bipolar rectangular voltages on the smooth muscle was examined.

The frequency range of the stimulating voltage was 0.005–500 Hz, changed with a step of 10 times (e.g. 0.005 Hz, 0.05 Hz, 0.5 Hz, etc.). Further, 3.0 cc of atropine was subsequently administered intravenously to block the cholinergic nerves and to determine whether the smooth muscle was stimulated directly, or the invoked contraction was a result from stimulating the cholinergic pathways.

When testing the concept of producing local non-propagated contractions on the 2 dogs, low frequency voltages (DC—0.5 Hz) failed to produce visible contraction regardless of the duration of the applied stimuli. Amplitudes above 5 V (peak-to-peak) were found to be dangerous for the tissue. Whitening of the tissue around the electrodes was noted when stimulating amplitudes were between 5–8 V, and higher amplitudes produced visible burns.

Stimulating voltages of 5, 50 and 500 Hz applied for 2–4 seconds produced quite strong local circumferential non-propagated contractions. Amplitudes up to 20 V did not produce visible damage to the tissue. The response of the smooth muscle to trains of rectangular impulses at 50 Hz (peak-to-peak amplitudes 10–20 V) was found to be preferable and always produced visibly strong local circumferential contraction between and slightly beyond the two stimulating electrodes.

Blocking the cholinergic neurotransmitters with 3.0 cc of atropine, however, abolished or dramatically reduced the significance of the invoked contractions in the whole frequency range of stimulation. The fact that after administering atropine the production of invoked contractions ceased regardless of the stimulating parameters may indicate that the cholinergic pathways were responsible for the invoked contractions. If these pathways are blocked, gastric electrical stimulation to facilitate gastric emptying may not be possible.

Thus, the testing conducted on the 2 dogs suggested that:
(a) the hypothesis that relatively high frequency bipolar voltage can be used for local "in vivo" stimulation of gastric smooth muscle is quite realistic;
(b) the response to stimulation with frequencies higher than 5 Hz is mainly cholinergic in nature and is abolished or significantly suppressed by atropine;
(c) stimulation with a train of 50 Hz rectangular impulses (peak-to-peak amplitude 10–20 V) for about 2–4 seconds can induce almost immediate, relatively strong non-propagated contractions.

Figure 3:
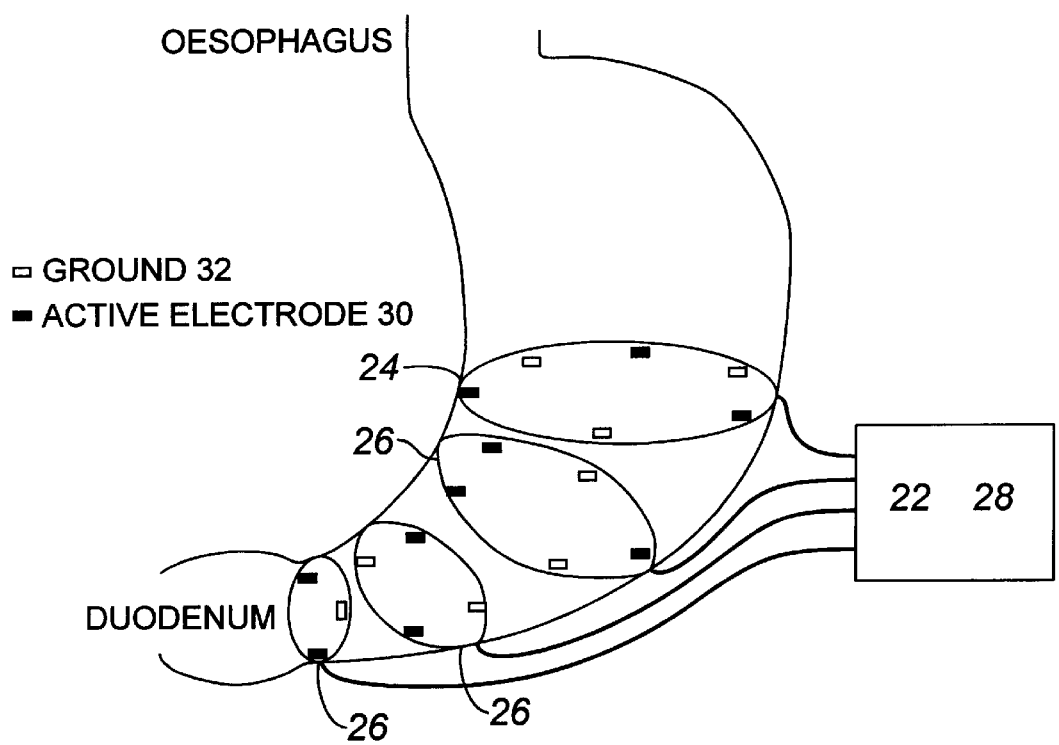
FIG. 3 is a schematic drawing of a canine stomach with 4 sets of circumferentially implanted electrodes in a second study conducted by the inventors.

The second study was conducted to determine if artificially propagated antral contractions could be produced by phase-locking the local circumferential electrical stimulation. In this study, six healthy anaesthetized dogs with similar dimensions (4 female, 2 male, body mass index [weight, kg/height, m] 26.4 (2.5 kg/m, weight 29.7 (3.8 kg) underwent laparotomy and implantation of pairs of locally designed bipolar stainless steel wire electrodes. Each pair consisted of 2 wires (10×0.25 mm, 3–4 cm apart) implanted subserosally in a circumferential position into the stomach wall. One to 4 electrode pairs were placed at approximately 1, 4.2, 7.8 and 11.7 cm proximally from the pylorus, as shown in FIG. 3. The interelectrode distance in each circumferential set was between 2.5 and 3.5 cm. One of the electrodes from each pair was connected to a common ground.

Figure 4:
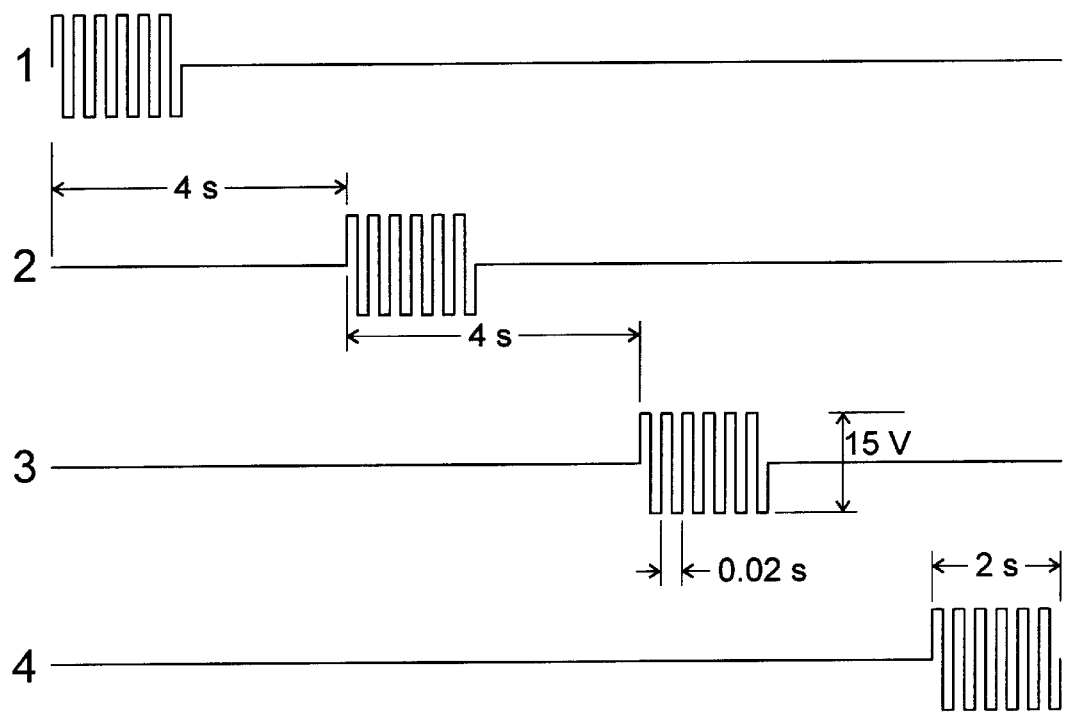
FIG. 4 shows the time characteristics of the stimuli applied to the electrode sets starting with the most proximal as shown in FIG. 3.

Computer modeling based on the previously described conoidal dipole model of gastric electrical activity predicted that propagated contractions could be produced circumferentially using at least 4 rings of stimulating electrodes implanted along the gastric circumference and supplied simultaneously with phase-locked bipolar 2-second trains of 50 Hz, 15 V (peak-to-peak) rectangular voltage. These stimulating parameters were applied to the 4 sets of circumferentially-implanted electrodes in the canine antrum, as shown in FIG. 4.

Bipolar voltage stimulation was attempted also at lower (0, 0.005, 0.05, 0.1, 0.2, 0.5, 1, 2, 3, 4, 5, 10, 20, 25, 30 and 40 Hz) and higher (500 Hz) frequencies using various peak-to-peak amplitudes. The stimuli were either phase-locked or independently applied to the individual electrode sets.

All electrical stimuli were applied during the estimated resting phase of the migrating myoelectrical complex in the fasting state. The duration of each stimulating session did not exceed 10 minutes.

After testing the effect of various stimuli during the basal state, the cholinergic pathways were blocked with intravenous administration of 3.0 cc of atropine and applied stimulation in the whole frequency/amplitude range for about ½ hour.

Gastric contractions and their propagation are clearly seen in a spontaneously contracting stomach at laparotomy, particularly in the active (third) phase of the migrating myoelectrical complex. Therefore, it was assumed that invoked contractile activity and its propagation (if any) could also be assessed visually during the stimulation sessions. Accordingly, force transducers were not implanted on the serosal wall.

Figure 5:
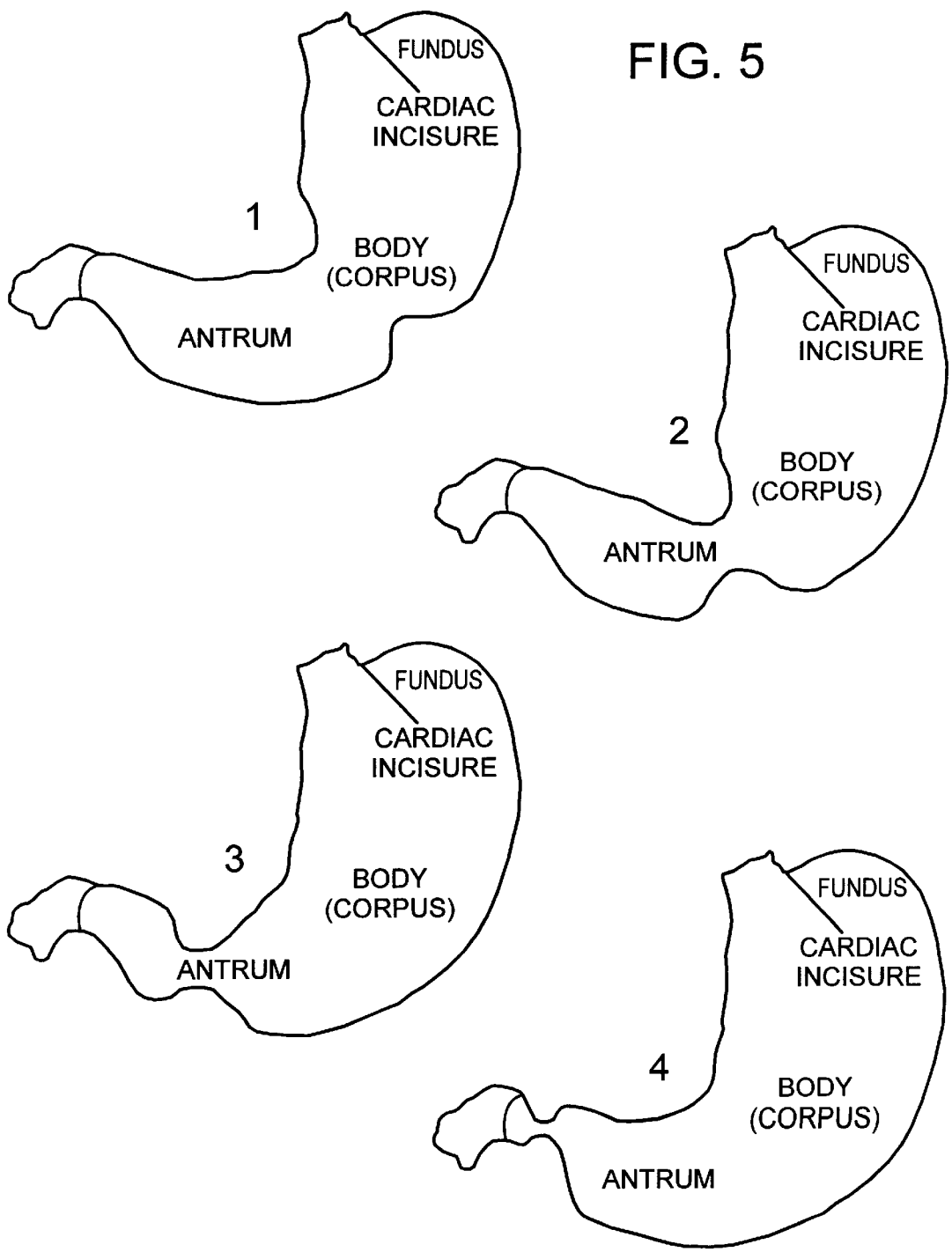
FIG. 5 is a schematic drawing of the 4 artificially invoked contracting phases obtained by phase-locking the stimulating voltage in the electrode sets shown in FIG. 3.

Using the parameters suggested by the conoidal computer model, clearly seen gastric contractions were produced which were propagated distally by phase-locking the stimulating voltage, as shown in FIG. 5. Spontaneous propagation of the contractile ring after applying the same stimuli to individual electrode sets was not observed.

When stimulating with 2-second trains of bipolar voltages above 5 Hz and peak-to-peak amplitudes 10–20 V, strong non-propagated circumferential contractions were observed without visible damage to the tissue surrounding the implanted electrodes. These invoked contractions could be artificially propagated from the area of one electrode set to the area of the other by phase-locking the stimulating voltages. The strength of these contractions reached its peak when stimulating at around 50 Hz (providing the peak-to-peak stimulating amplitude was kept the same).

When stimulating with voltages below 5 Hz and a peak-to-peak amplitude range of 10–20 V, visible damage to the tissue around the electrodes was noted which required a reduction in the amplitude of the stimuli and reimplant of the electrodes. Reduction of the peak-to-peak voltage to 5–8 V was associated with whitening of the tissue surrounding the electrodes (the damage to the tissue was milder). No visible contractions were produced after reimplanting the electrodes and reducing the peak-to-peak amplitudes below 5 V.

Stimulation with higher frequency (500 Hz, 10–20 V peak-to-peak) also produced visible circumferential contractions, but they were estimated to be slightly weaker than the contractions produced with stimulating voltage of 50 Hz and the same amplitude range.

Blocking the cholinergic pathways with 3.0 cc of atropine abolished the ability to produce invoked contractions regardless of the frequencies and the amplitudes of the applied stimuli.

As indicated by the second study, stimulating the canine smooth muscle with higher frequencies caused the muscle to respond before the tissue surrounding the implanted electrodes got visibly damaged. The best response was observed at 50 Hz, and peak-to-peak amplitude of 10–20 V seemed to be tolerable. It is possible that the smooth muscle stimulated with bipolar voltage starts to respond to slightly lower stimulating frequencies than when stimulated monopolarly. A circumferential arrangement of the individual electrodes is also preferred, as is the utilization of 4 circumferential electrode sets which are successively positioned in a proximal direction starting from the pyloric region. By phase-locking the applied stimuli between the successive electrode sets (starting this time from the most proximal set) the contraction could be artificially propagated distally.

Figure 6:
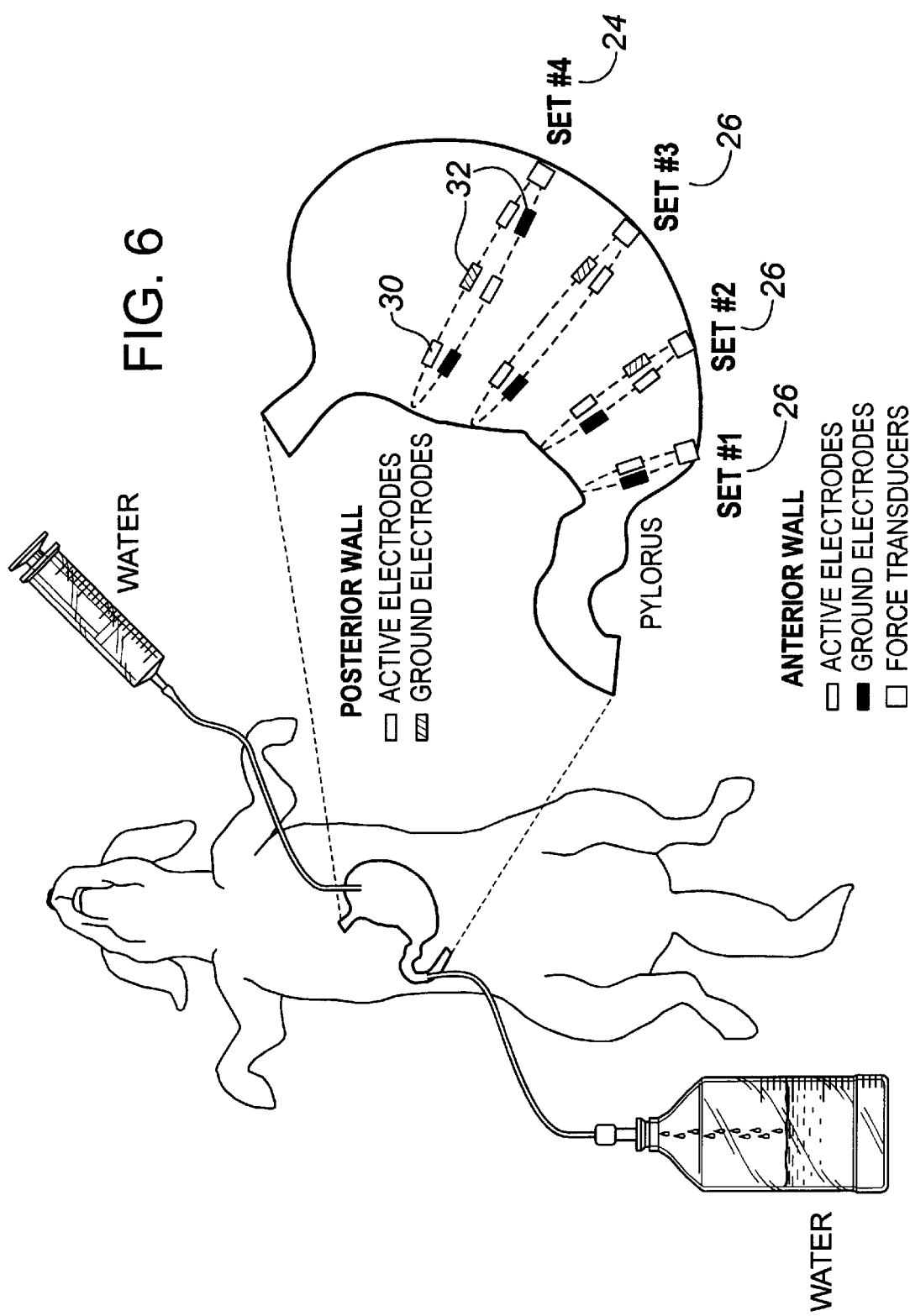
FIG. 6 is a schematic drawing of a canine stomach with 4 sets of circumferentially implanted electrodes in a third study conducted by the inventors.

In the third study, eight healthy anaesthetized dogs with similar dimensions (5 male, 3 female, body mass index [weight, kg/(height, m)$^2$] 11.6+/31 2.8 kg/m$^2$, weight 18.5+/−3.9 kg) underwent laparotomy and implantation of bipolar stainless steel wire electrodes. Each electrode was a stainless steel wire (10×0.25 mm). Four sets of electrodes were inserted at approximately 2, 6, 10 and 14 cm from the pylorus. Each set consisted of 2 (the most distal set) to 6 electrodes (the most proximal set) inserted under the gastric serosa in a circumferential fashion as shown in FIG. 6. The interelectrode distance in each set was between about 2.5 and 3.5 cm. Every alternate electrode in each electrode set was connected to a common ground. All four sets of wires were connected to a microprocessor-controlled digital stimulator (4-channel 12-bit digital-to-analog converter with up to 6.5 mA current output per channel, controlled by specially designed software on an IBM 486-33 personal computer). In 4 of the dogs, 4 force transducers (RB Products, Madison, Wis.) were implanted close to each circumferential electrode set.

Computer modeling based upon the conoidal model indicated that propagated contractions could be produced circumferentially using 4 rings of stimulating electrodes implanted along the gastric circumference and supplied simultaneously with phase-locked bipolar trains of 50 Hz, 15 V (peak to peak) rectangular voltage and time period between one cycle of the application of the stimulus to all electrode sets and the next cycle of 16 seconds. In this third study, the time period of the cycle of application of the stimulus was increased to 32 seconds and the peak to peak amplitude of the stimulating trains was reduced to 14 V, as shown in FIG. 7.

Stimulated and spontaneous gastric emptying of liquid contents were compared. A large bore plastic tube (diameter 0.5 cm) was introduced into the apex of the gastric fundus in order to fill the stomach with water. Another tube (diameter 1.5 cm) was positioned in the descending duodenum and the duodenum occluded distal to it. The stomach was filled with 600–800 cc of water. The times to empty 200 ml of water (the estimated amount in the antrum) was compared with and without stimulation. After each emptying session, 200 ml of water were added to the stomach so that the volume of water in the stomach remained the same before each measurement. The tests were repeated at random 3 times per dog. The results for the emptying times were averaged and a single mean value and its standard deviation were obtained for each dog. The two sets of half-emptying times (T1/2 obtained using stimulation, and through spontaneous emptying) were statistically examined using a standard Chi-square test for significance with the spontaneous emptying mean half-times being the expected values.

In addition, a test was performed on a 32 year old female patient diagnosed with severe gastroparesis who was undergoing laparotomy and gastrectomy. A set of 4 circumferential electrodes (2 active and 2 grounds) similar to set number 3 shown in FIG. 6 was implanted about 8–10 cm proximal to the pylorus and a stimulating voltage with the characteristics shown in Channel 3 of FIG. 7 was applied. The circumferential electrodes were not implanted permanently and gastric emptying tests were not performed.

Figure 7:
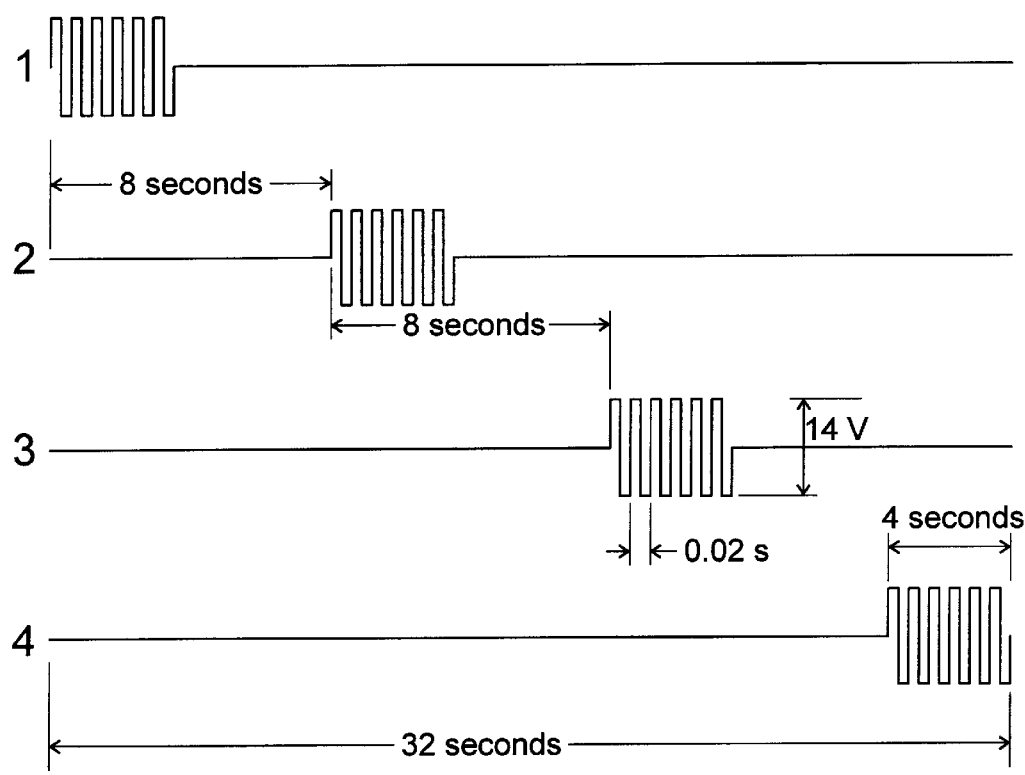
FIG. 7 shows the phase-locking of the electrical stimuli applied to the electrode sets shown in FIG. 6.

Using 14 V/50 Hz rectangular trains each having an interval or duration of 4 seconds, followed by an equivalent interval or pause of 4 seconds, as shown in FIG. 7, clearly seen gastric contractions were produced and artificially propagated distally by phase-locking the electrical stimulus. In this study, the stimulating voltage was phase-locked and the total stimulating current drawn from each electrode set increased gradually in a proximal direction from approximately 1–1.5 mA (for the most distal set) to 6–6.5 mA (for the most proximal set).

Figure 9:
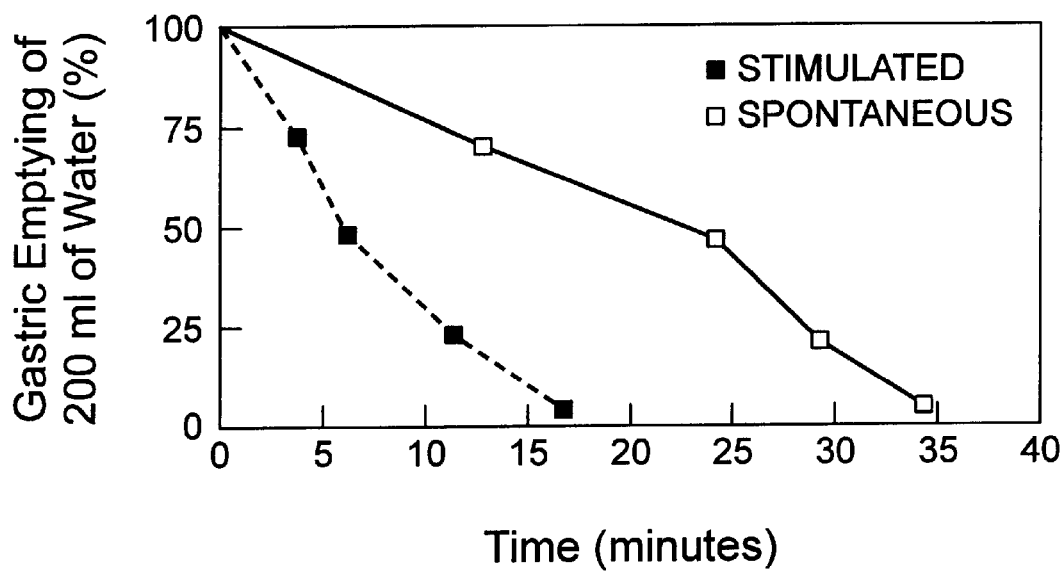
FIG. 9 is a graphical representation of a typical example of gastric emptying rates with and without electrical stimulation.

The invoked artificially propagated circumferential contractions moved liquid content into the duodenum synchronously with the period of repetition of the stimulating trains. Stimulated mean half-emptying times for each dog were significantly lower than spontaneous mean half-emptying times ($p<0.001$, FIGS. 8 and 9). The averages of overall mean half-times for gastric emptying of water were 25.28+/−12.9 minutes without stimulation and 6.72+/−3.0 minutes with stimulation. FIG. 9 shows a typical example of gastric emptying rates with and without electrical stimulation.

Using similar stimulating parameters to the ones from FIG. 7 (Channel 3), visibly strong circumferential contractions were also produced in the stomach of the gastroparetic patient.

What is claimed is:

1. A device for electrical stimulation of smooth muscle comprising a portion of the gastro-intestinal tract, wherein the portion of the gastro-intestinal tract defines a longitudinal axis extending therethrough, the device comprising:

(a) a proximal electrode set for arrangement circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set, wherein the proximal electrode set is comprised of at least one active electrode and at least one ground electrode;

(b) at least one distal electrode set for arrangement circumferentially about the portion of the gastrointestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set, wherein each distal electrode set is comprised of at least one active electrode and at least one ground electrode;

(c) at least one power source for providing an electrical stimulus to the proximal and distal electrode sets sufficient to stimulate the smooth muscle to produce the local circumferential contractions;

(d) a timing mechanism, associated with the power source, for phase locking the electrical stimulus such that the electrical stimulus is applied to the proximal and distal electrode sets successively and repetitively;

wherein the axially spaced relationship between the electrode sets and the timing of the electrical stimulus applied to the electrode sets are selected such that the local circumferential contractions are artificially propagated distally through the portion of the gastro-intestinal tract.

2. The device as claimed in claim 1 wherein the portion of the gastro-intestinal tract is comprised of the esophagus, the stomach, the small intestine, the large intestine, the anal sphincter and combinations thereof.

3. The device as claimed in claim 2 wherein the portion of the gastro-intestinal tract is comprised of the stomach.

4. The device as claimed in claim 3 comprising at least three distal electrode sets located distally to the proximal electrode set and in an axially spaced relationship with each other such that the phase-locked electrical stimulus produces a local circumferential contraction at the proximal electrode set and each distal electrode set in succession.

5. The device as claimed in claim 4 comprising three distal electrode sets.

6. The device as claimed in claim 4 wherein the artificial propagation of local contractions through the stomach is sufficient to facilitate at least a partial emptying thereof.

7. The device as claimed in claim 6 wherein the proximal electrode set is located in about the mid-corpus of the stomach.

8. The device as claimed in claim 1 wherein the active electrodes are connected to the power source in a manner such that the electrical stimulus is provided concurrently to each of the active electrodes included in an electrode set.

9. The device as claimed in claim 3 wherein the distance between the electrodes in each of the proximal and distal electrode sets is between about 2 to 4 centimeters.

10. The device as claimed in claim 9 wherein the number of active electrodes is greater than or equal to the number of ground electrodes in each of the proximal and distal electrode sets.

11. The device as claimed in claim 9 wherein the electrical stimulus is provided by an alternating current source.

12. The device as claimed in claim 11 wherein the alternating current source is a bipolar alternating current source.

13. The device as claimed in claim 12 wherein the alternating current source is a rectangular alternating current source or a square alternating current source.

14. The device as claimed in claim 13 wherein the frequency of the alternating current source is between about 5 to 500 Hertz.

15. The device as claimed in claim 14 wherein the frequency of the alternating current source is between about 5 to 50 Hertz.

16. The device as claimed in claim 15 wherein the frequency of the alternating current source is about 50 Hertz.

17. The device as claimed in claim 16 wherein the voltage provided by the alternating current source is less than or equal to about 20 Volts, peak to peak.

18. The device as claimed in claim 17 wherein the voltage provided by the alternating current source is between about 10 to 20 Volts, peak to peak.

19. The device as claimed in claim 18 wherein the voltage provided by the alternating current source is between about 14 to 15 Volts, peak to peak.

20. The device as claimed in claim 18 wherein the timing mechanism applies the electrical stimulus such that the electrical stimulus is applied to the electrode set for an interval of between about 2 to 4 seconds, following which there is an equivalent interval of no stimulation before the application of the electrical stimulus to the next successive electrode set.

21. A method for electrical stimulation of smooth muscle comprising a portion of the gastro-intestinal tract, wherein the portion of the gastro-intestinal tract defines a longitudinal axis extending therethrough and wherein the method is performed using a device comprised of a proximal electrode set and at least one distal electrode set, the method comprising the steps of:

(a) arranging the proximal electrode set circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) arranging each of the distal electrode sets circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) applying an electrical stimulus to the proximal and distal electrode sets sufficient to stimulate the smooth muscle to produce the local circumferential contractions, wherein the electrical stimulus is phase-locked such that the electrical stimulus is applied to the proximal and distal electrode sets successively and repetitively;

wherein the axially spaced relationship between the electrode sets and the timing of the phase-locking of the electrical stimulus applied to the electrode sets are selected such that the local circumferential contractions are artificially propagated distally through the portion of the gastro-intestinal tract.

22. The method as claimed in claim 21 wherein the portion of the gastro-intestinal tract is comprised of the esophagus, the stomach, the small intestine, the large intestine, the anal sphincter and combinations thereof.

23. The method as claimed in claim 22 wherein the portion of the gastro-intestinal tract is comprised of the stomach.

24. The method as claimed in claim 23 wherein the proximal and distal electrode sets are implanted subserosally in the stomach.

25. The method as claimed in claim 24 wherein the device is comprised of at least three distal electrode sets and wherein the distal electrode sets are arranged distally to the proximal electrode set and in an axially spaced relationship with each other such that the phase-locked electrical stimulus produces a local circumferential contraction at the proximal electrode set and at each distal electrode set in succession.

26. The method as claimed in claim 25 wherein the device is comprised of three distal electrode sets.

27. The method as claimed in claim 25 wherein the artificial propagation of local contractions through the stomach is sufficient to facilitate at least a partial emptying thereof.

28. The method as claimed in claim 27 wherein the proximal electrode set is arranged in about the mid-corpus of the stomach.

29. The method as claimed in claim 27 wherein each of the proximal and distal electrode sets of the device is comprised of at least one active electrode and at least one ground electrode and wherein the electrical stimulus is applied to the active electrodes in a manner such that the electrical stimulus is applied concurrently to each of the active electrodes included in an electrode set.

30. The method as claimed in claim 29 wherein the distance between the electrodes in each of the proximal and distal electrode sets is between about 2 to 4 centimeters.

31. The method as claimed in claim 30 wherein the number of active electrodes is greater than or equal to the number of ground electrodes in each of the proximal and distal electrode sets.

32. The method as claimed in claim 30 wherein the electrical stimulus applied to the proximal and distal electrode sets is alternating.

33. The method as claimed in claim 32 wherein the alternating electrical stimulus is bipolar.

34. The method as claimed in claim 33 wherein the shape of the alternating electrical stimulus is rectangular or square.

35. The method as claimed in claim 34 wherein the frequency of the alternating electrical stimulus is between about 5 to 500 Hertz.

36. The method as claimed in claim 35 wherein the frequency of the alternating electrical stimulus is between about 5 to 50 Hertz.

37. The method as claimed in claim 36 wherein the frequency of the alternating electrical stimulus is about 50 Hertz.

38. The method as claimed in claim 37 wherein the voltage of the alternating electrical stimulus is less than or equal to about 20 Volts, peak to peak.

39. The method as claimed in claim 38 wherein the voltage of the alternating electrical stimulus is between about 10 to 20 Volts, peak to peak.

40. The method as claimed in claim 39 wherein the voltage of the alternating electrical stimulus is between about 14 to 15 Volts, peak to peak.

41. The method as claimed in claim 39 wherein the electrical stimulus is applied to the electrode set for an interval of between about 2 to 4 seconds, following which there is an equivalent interval of no stimulation before the application of the electrical stimulus to the next successive electrode set.

42. A method for electrical stimulation of smooth muscle comprising a portion of the gastro-intestinal tract, wherein the portion of the gastro-intestinal tract defines a longitudinal axis extending therethrough, the method comprising the steps of:
   (a) applying an electrical stimulus at a proximal location to the smooth muscle circumferentially about the portion of the gastro-intestinal tract in a plane substantially perpendicular to the longitudinal axis, wherein the electrical stimulus is sufficient to stimulate the smooth muscle to produce a local circumferential contraction at the proximal location;
   (b) applying an electrical stimulus at at least one distal location to the smooth muscle circumferentially about the portion of the gastro-intestinal tract in a plane substantially perpendicular to the longitudinal axis, wherein the distal location is in axially spaced relationship relative to the proximal location and wherein the electrical stimulus is sufficient to stimulate the smooth muscle to produce a local circumferential contraction at the distal location; and
   (c) phase-locking the electrical stimulus applied at the proximal and distal locations such that the electrical stimulus is applied at the proximal and distal locations successively and repetitively;
wherein the axially spaced relationship between the proximal and distal locations and the timing of the phase-locking of the electrical stimulus applied to the locations are selected such that the local circumferential contractions are artificially propagated distally through the portion of the gastro-intestinal tract.

43. The method as claimed in claim 42 wherein the portion of the gastro-intestinal tract is comprised of the esophagus, the stomach, the small intestine, the large intestine, the anal sphincter and combinations thereof.

44. The method as claimed in claim 43 wherein the portion of the gastro-intestinal tract is comprised of the stomach.

45. The method as claimed in claim 44 wherein the electrical stimulus is applied at the proximal and distal locations subserosally in the stomach.

46. The method as claimed in claim 45 wherein the electrical stimulus is applied at at least three distal locations and wherein the distal locations are located distally to the proximal location and in an axially spaced relationship with each other such that the phase-locking of the electrical stimulus produces a local circumferential contraction at the proximal location and each distal location in succession.

47. The method as claimed in claim 46 wherein the electrical stimulus is applied at three distal locations.

48. The method as claimed in claim 46 wherein the artificial propagation of local contractions through the stomach is sufficient to facilitate at least a partial emptying thereof.

49. The method as claimed in claim 48 wherein the proximal location is located in about the mid-corpus of the stomach.

50. The method as claimed in claim 48 wherein the electrical stimulus applied at the proximal and distal locations is alternating.

51. The method as claimed in claim 50 wherein the alternating electrical stimulus is bipolar.

52. The method as claimed in claim 51 wherein the shape of the alternating electrical stimulus is rectangular or square.

53. The method as claimed in claim 52 wherein the frequency of the alternating electrical stimulus is between about 5 to 500 Hertz.

54. The method as claimed in claim 53 wherein the frequency of the alternating electrical stimulus is between about 5 to 50 Hertz.

55. The method as claimed in claim 54 wherein the frequency of the alternating electrical stimulus is about 50 Hertz.

56. The method as claimed in claim 55 wherein the voltage of the alternating electrical stimulus is less than or equal to about 20 Volts, peak to peak.

57. The method as claimed in claim 56 wherein the voltage of the alternating electrical stimulus is between about 10 to 20 Volts, peak to peak.

58. The method as claimed in claim 57 wherein the voltage of the alternating electrical stimulus is between about 14 to 15 Volts, peak to peak.

59. The method as claimed in claim 57 wherein the electrical stimulus is phase-locked such that the electrical stimulus is applied to the location for an interval of between about 2 to 4 seconds, following which there is an equivalent interval of no stimulation before the application of the electrical stimulus to the next successive location.

* * * * *

UNITED STATES PATENT AND TRADEMARK OFFICE
CERTIFICATE OF CORRECTION

PATENT NO.    : 6,243,607 B1
DATED         : June 5, 2001
INVENTOR(S)   : Martin P. Mintchev et al.

It is certified that error appears in the above-identified patent and that said Letters Patent is hereby corrected as shown below:

Column 3,
Line 8, in Equation [1] change "$\pi$" to -- p --; change "$\delta$" to -- d --;
Line 38, in Equation [3] change "$\pi$" to -- p --; change "$\epsilon$" to -- e --;

change " $\int_{(g)}$ " to --(s)--; change "$D\dot{}\rho$" to --D.r--, change "$|\rho|^3$" to --|r|3--.

Column 12,
Line 22, change "Equation[1]" to -- Equation [4] --.

Line 52, in Equation [5] change " $\sum_{t}$ { " to --(t{--.

Column 19,
Line 36, change "+/31 2.8kg/m$^2$" to -- +/-2.8 kg/m$^2$ --.

Column 21,
Line 21, change "1" to -- 8 --

Signed and Sealed this

Twenty-seventh Day of August, 2002

Attest:

JAMES E. ROGAN
Attesting Officer    Director of the United States Patent and Trademark Office